(12) United States Patent
Boyden et al.

(10) Patent No.: US 8,147,537 B2
(45) Date of Patent: *Apr. 3, 2012

(54) RAPID-PROTOTYPED CUSTOM-FITTED BLOOD VESSEL SLEEVE

(75) Inventors: Edward S. Boyden, Cambridge, MA (US); Ralph G. Dacey, Jr., St. Louis, MO (US); Colin P. Derdeyn, St. Louis, MO (US); Joshua L. Dowling, Webster Groves, MO (US); Roderick A. Hyde, Redmond, WA (US); Muriel Y. Ishikawa, Livermore, CA (US); Eric C. Leuthardt, St. Louis, MO (US); Nathan P. Myhrvold, Medina, WA (US); Clarence T. Tegreene, Bellevue, WA (US); Lowell L. Wood, Jr., Bellevue, WA (US); Victoria Y. H. Wood, Livermore, CA (US); Gregory J. Zipfel, St. Louis, MO (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1084 days.

This patent is subject to a terminal disclaimer.

(21) Appl. No.: 11/880,434

(22) Filed: Jul. 19, 2007

(65) Prior Publication Data

US 2008/0082160 A1 Apr. 3, 2008

Related U.S. Application Data

(63) Continuation-in-part of application No. 11/454,343, filed on Jun. 16, 2006, and a continuation-in-part of application No. 11/455,010, filed on Jun. 16, 2006, and a continuation-in-part of application No. 11/526,089, filed on Sep. 22, 2006, and a continuation-in-part of application No. 11/526,144, filed on Sep. 22, 2006, and a continuation-in-part of application No. 11/526,201, filed on Sep. 22, 2006, and a continuation-in-part of application No. 11/526,203, filed on Sep. 22, 2006, now Pat. No. 7,769,603, and a continuation-in-part of application No. 11/541,377, filed on Sep. 29, 2006, and a continuation-in-part of application No. 11/541,378, filed on Sep. 29, 2006, and a continuation-in-part of application No. 11/541,448, filed on Sep. 29, 2006, and a continuation-in-part of application No. 11/541,452, filed on Sep. 29, 2006, and a continuation-in-part of application No. 11/541,492, filed on Sep. 29, 2006, and a continuation-in-part of application No. 11/879,751, filed on Jul. 17, 2007.

(51) Int. Cl.
*A61F 2/06* (2006.01)
*G06Q 10/00* (2006.01)
*G06Q 50/00* (2006.01)
*A61M 29/00* (2006.01)

(52) U.S. Cl. .............. 623/1.13; 705/2; 705/3; 623/1.15; 623/1.16; 606/200

(58) Field of Classification Search .................. 705/2–3; 623/1.15–1.16, 1.13; 606/200
See application file for complete search history.

(56) References Cited

U.S. PATENT DOCUMENTS 4,460,642 A 7/1984 Errede et al.
(Continued)

OTHER PUBLICATIONS

R. Courbier, et al., Progress in the Treatment of Anastomotic Aneurysms, 1988, World Journal of Surgery, 12, pp. 742-749.*

(Continued)

*Primary Examiner* — Jason Dunham
*Assistant Examiner* — Amber Altschul

(57) ABSTRACT

Methods, apparatuses, computer program products, devices and systems are described that include a rapid-prototyped blood vessel sleeve that is custom-fitted for a blood vessel at least partly based on anatomical blood vessel data from an individual.

32 Claims, 11 Drawing Sheets

U.S. PATENT DOCUMENTS

| | | | |
|---|---|---|---|
| 4,496,535 A | 1/1985 | Gould et al. | |
| 4,575,805 A | 3/1986 | Moermann et al. | |
| 4,872,867 A | 10/1989 | Joh | |
| 5,163,007 A | 11/1992 | Slilaty | |
| 5,163,952 A | 11/1992 | Froix | |
| 5,258,020 A | 11/1993 | Froix | |
| 5,407,431 A | 4/1995 | Botich et al. | |
| 5,554,180 A | 9/1996 | Turk | |
| 5,683,449 A | 11/1997 | Marcade | |
| 5,733,868 A | 3/1998 | Peterson et al. | |
| 5,823,948 A | 10/1998 | Ross, Jr. et al. | |
| 5,850,222 A | 12/1998 | Cone | |
| 5,954,701 A | 9/1999 | Matalon | |
| 5,966,693 A | 10/1999 | Burgess | |
| 5,966,963 A | 10/1999 | Kovalaske | |
| 6,149,433 A | 11/2000 | Ziegler et al. | |
| 6,221,447 B1 | 4/2001 | Munn et al. | |
| 6,231,514 B1 | 5/2001 | Lowe et al. | |
| 6,458,153 B1* | 10/2002 | Bailey et al. | 623/1.24 |
| 6,464,687 B1* | 10/2002 | Ishikawa et al. | 604/891.1 |
| 6,481,262 B2 | 11/2002 | Ching et al. | |
| 6,532,964 B2* | 3/2003 | Aboul-Hosn et al. | 128/898 |
| 6,569,104 B2 | 5/2003 | Ono et al. | |
| 6,592,565 B2 | 7/2003 | Twardowski | |
| 6,592,605 B2 | 7/2003 | Lenker et al. | |
| 6,663,765 B2 | 12/2003 | Cherkes | |
| 6,685,738 B2* | 2/2004 | Chouinard et al. | 623/1.15 |
| 6,726,696 B1 | 4/2004 | Houser et al. | |
| 6,726,923 B2 | 4/2004 | Iyer et al. | |
| 6,754,357 B2 | 6/2004 | McIntosh et al. | |
| 6,780,510 B2 | 8/2004 | Ogle et al. | |
| 6,793,668 B1 | 9/2004 | Fisher | |
| 6,951,053 B2 | 10/2005 | Padilla et al. | |
| 6,996,245 B2 | 2/2006 | Hanna | |
| 7,326,240 B1 | 2/2008 | Caro et al. | |
| 7,371,067 B2 | 5/2008 | Anderson et al. | |
| 7,804,991 B2* | 9/2010 | Abovitz et al. | 382/128 |
| 2001/0025131 A1 | 9/2001 | Edwin et al. | |
| 2001/0039504 A1 | 11/2001 | Linberg et al. | |
| 2002/0006401 A1 | 1/2002 | Rogers et al. | |
| 2002/0023843 A1 | 2/2002 | Cherkes | |
| 2002/0026944 A1* | 3/2002 | Aboul-Hosn et al. | 128/898 |
| 2002/0035555 A1 | 3/2002 | Wheeler et al. | |
| 2002/0068968 A1 | 6/2002 | Hupp | |
| 2002/0183628 A1 | 12/2002 | Reich et al. | |
| 2002/0198587 A1 | 12/2002 | Greenberg et al. | |
| 2003/0018294 A1 | 1/2003 | Cox | |
| 2003/0060782 A1 | 3/2003 | Bose et al. | |
| 2003/0149335 A1 | 8/2003 | Silverman et al. | |
| 2003/0200120 A1 | 10/2003 | Binkert | |
| 2004/0024443 A1 | 2/2004 | Dwyer et al. | |
| 2004/0093105 A1 | 5/2004 | Holloway et al. | |
| 2004/0149294 A1 | 8/2004 | Gianchandani et al. | |
| 2004/0204751 A1 | 10/2004 | Fischell et al. | |
| 2004/0230131 A1 | 11/2004 | Kassab et al. | |
| 2005/0037133 A1 | 2/2005 | Halleriet et al. | |
| 2005/0038342 A1* | 2/2005 | Mozayeni et al. | 600/454 |
| 2005/0049691 A1 | 3/2005 | Mericle et al. | |
| 2005/0061336 A1 | 3/2005 | Goetz et al. | |
| 2005/0096498 A1 | 5/2005 | Houser et al. | |
| 2005/0107817 A1 | 5/2005 | White et al. | |
| 2005/0107867 A1 | 5/2005 | Taheri | |
| 2005/0203457 A1 | 9/2005 | Smego | |
| 2005/0251183 A1 | 11/2005 | Buckman et al. | |
| 2005/0267569 A1 | 12/2005 | Barrett et al. | |
| 2005/0273157 A1 | 12/2005 | Pinchasik | |
| 2005/0288763 A1 | 12/2005 | Andreas et al. | |
| 2006/0058638 A1 | 3/2006 | Boese et al. | |
| 2006/0069426 A1 | 3/2006 | Weinberger | |
| 2006/0079740 A1 | 4/2006 | Silver et al. | |
| 2006/0122697 A1 | 6/2006 | Shanley et al. | |
| 2006/0129228 A1 | 6/2006 | Golesworthy et al. | |
| 2006/0178551 A1 | 8/2006 | Melvin | |
| 2006/0206038 A1 | 9/2006 | Jenkins et al. | |
| 2006/0280351 A1 | 12/2006 | Luping et al. | |
| 2007/0021816 A1 | 1/2007 | Rudin | |
| 2007/0051366 A1 | 3/2007 | Hansmann et al. | |
| 2007/0083258 A1 | 4/2007 | Falotico et al. | |
| 2007/0112581 A1 | 5/2007 | Smith et al. | |
| 2007/0118243 A1 | 5/2007 | Schroeder et al. | |
| 2008/0015677 A1 | 1/2008 | Glossop et al. | |
| 2008/0030497 A1 | 2/2008 | Hu et al. | |
| 2008/0234831 A1 | 9/2008 | Clarke et al. | |
| 2008/0243284 A1 | 10/2008 | Grishaber et al. | |
| 2009/0099652 A1 | 4/2009 | Granada et al. | |

OTHER PUBLICATIONS

PCT International Search Report; International App. No. PCT/US2008/008813; Jan. 9, 2009; pp. 1-2.
U.S. Appl. No. 11/541,492, Jung et al.
U.S. Appl. No. 11/541,452, Jung et al.
U.S. Appl. No. 11/541,448, Jung et al.
U.S. Appl. No. 11/541,378, Jung et al.
U.S. Appl. No. 11/541,377, Jung et al.
U.S. Appl. No. 11/526,203, Jung et al.
U.S. Appl. No. 11/526,201, Jung et al.
U.S. Appl. No. 11/526,144, Jung et al.
U.S. Appl. No. 11/526,089, Jung et al.
U.S. Appl. No. 11/455,010, Jung et al.
U.S. Appl. No. 11/454,343, Jung et al.
Bertolero, Art; Ibrahim, Tamer; Geyster, Steve; "Ventricular Restoration"; pp. 1-10.
Billinger, M.; Buddeberg, F.; Hubbell, J. A.; Elbert, D. L.; Schaffner, T.; Mettler, D.; Windecker, S.; Meier, B.; Hess O. M.; "Polymer Stent Coating For Prevention Of Neointimal Hyperplasia"; The Journal Of Invasive Cardiology; bearing a date of Sep. 2006; printed on Jul. 16, 2007; pp. 423-426; vol. 18; No. 9.
"Human Arterial Tree Project"; Jun. 5, 2007; pp. 1-16; located at http://www.cfm.brown.edu/crunch/ATREE/.
"Intellectual Property"; Patent Disclosure Form; bearing a date of Sep. 2, 2003; pp. 1-9; Case #CHFT-MRI-01.
Istook, Cynthia L.; "Rapid Prototyping in the Textile & Apparel Industry: A Pilot Project"; Journal Of Textile And Apparel, Technology And Management; Sep. 2000; pp. 1-14; vol. 1, No. 1; NC State University.
Kaufman, John A.; Brewster, David C.; Geller, Stuart C.; Fan, Chieh-Min; Cambria, Richard P.; Abbott, William A.; Waltman, Arthur C.; "Custom Bifurcated Stent-Graft for Abdominal Aortic Aneurysms: Initial Experience"; Journal Of Vascular And Interventional Radiology; 1999; pp. 1099-1106; vol. 10; No. 8; Society Of Cardiovascular And Interventional Radiology.
"Press Release: SurModics Provides Hydrophilic Coating on Xtent's Drug-Eluting Stent Delivery System"; Business Wire: Financial News; bearing a date of May 15, 2006; pp. 1-2; Yahoo! Inc.
"Rapid Protyping Technology"; DRM Associates; printed on Jun. 26, 2007; pp. 1-2; located at http://www.npd-solutions.com/rp.html.
"Scalable Visualization Application Framework, amira 4 Datasheet"; Mercury Computer Systems, Inc.; pp. 1-12; located at www.mc.com.
"'Sleeve' Keeps Blockages At Bay—Research Shows Gortex Sleeves Wrapped Around Arteries Can Prevent Plaque Formations From Forming—Brief Article"; USA Today (Society For The Advancement Of Education); Feb. 1998; pp. 1; located at http://findarticles.com/p/articles/mi_m1272/is_n2633_v126/ai_20305717.
"Tracking Acute Myocardial Infarction: The First Step in Treating Ischemic CHF"; CHFT Proposal; bearing a date of 1999; pp. 1-4; American College of Cardiology and American Heart Association, Inc.
Tropea, Bradford I.; Schwarzacher, Severin P.; Chang, Albert; Asvar, Chris; Huie, Phil; Sibley, Richard K.; Zarins, Christopher K.; "Reduction Of Aortic Wall Motion Inhibits Hypertension-Mediated Experimental Atherosclerosis"; Journal Of The American Heart Association; 2000; pp. 2127-2133; vol. 20; American Heart Association.
Twardowski, Z.J.; Haynie, J.D.; "Measurements of Hemodialysis Catheter Blood Flow in Vivo"; The International Journal of Artificial Organs; bearing a date of 2002; pp. 276-280; vol. 25, No. 4; Wichtig Editore.
Twardowski, Z.J.; Seger, R.M.; "Dimensions of Central Venous Structures in Humans Measured in Vivo Using Magnetic Resonance Imaging: Implications for Central-Vein Catheter Dimensions"; The International Journal of Artificial Organs; bearing a date of 2002; pp. 107-123; vol. 25, No. 2; Wichtig Editore.

Van Der Giessen, Willem J., PhD., MD; Van Beusekom, Heleen M.M.; Larsson, Rolf; Serruys, Patrick W., PhD., MD; "Heparin-Coated Coronary Stents"; Current Interventional Cardiology Reports; bearing a date of 1999; pp. 234-240; vol. 1; Current Science Inc.

"Vector-Based 3D Modeling, Imaging & Measurement, 3D-Doctor"; Able Software Corp.; pp. 1-13; located at www.3D-doctor.com.

Waugh, Alice C.; "Multidisciplinary Science May Yield New Drug Therapy"; MIT Tech Talk; bearing a date of May 18, 1994; printed on Jun. 4, 2007; pp. 1-2; vol. 38; No. 33; Massachusetts Institute of Technology.

Winder, R. J.; Sun, Z.; Kelly, B.; Ellis, P. K.; Hirst, D.; "Abdominal Aortic Aneurysm And Stent Graft Phantom Manufactured By Medical Rapid Prototyping"; Journal Of Medical Engineering & Technology; Mar./Apr. 2002; pp. 75-78; vol. 26; No. 2; Taylor & Francis Health Sciences.

"Xtent Custom I Trial Shows Zero Restenosis, Favorable Late Loss Results at Eight Months"; Healthcare Sales & Marketing Network NewsFeed; bearing a date of May 16, 2006; pp. 1-2.

"Xtent Customized Stent System Achieves Two Coronary Firsts: Single Catheter Delivers Multiple Stents and Longest Stent Ever Placed"; News & Information About Minimally Invasive Medicine; bearing dates of 1996-2006 and Jan. 5, 2006; pp. 1-2; Venture Digital LLC.

U.S. Appl. No. 12/804,897, Edward K.Y. Jung et al.

U.S. Appl. No. 13/135,437, Jung et al.

\* cited by examiner

FIG. 3
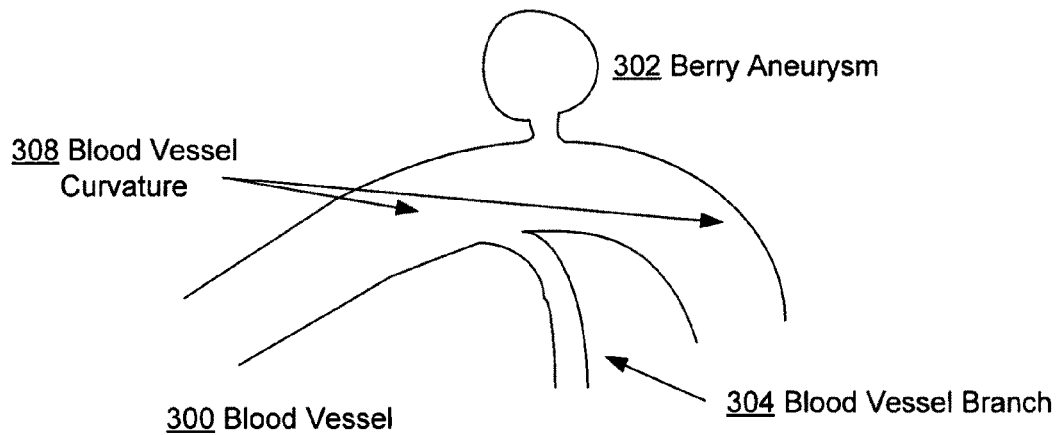
FIG. 3A
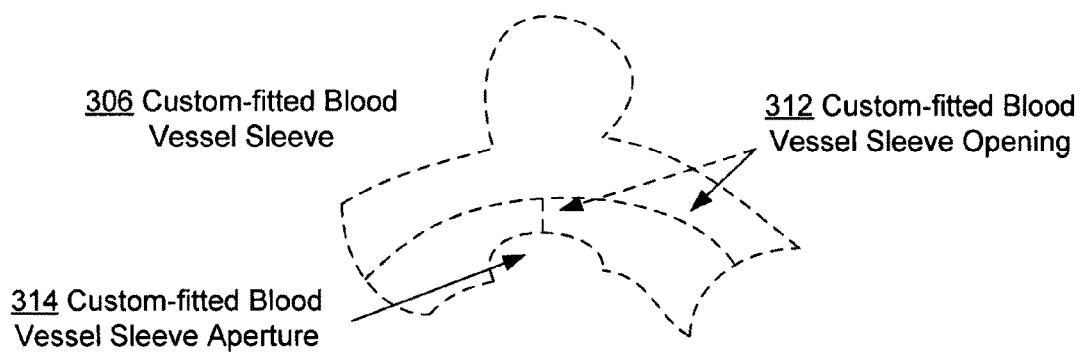
FIG. 3B
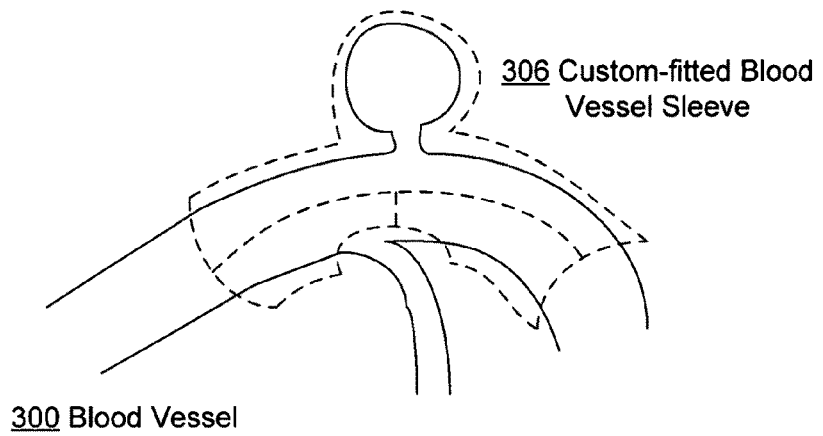
FIG. 3C

FIG. 4
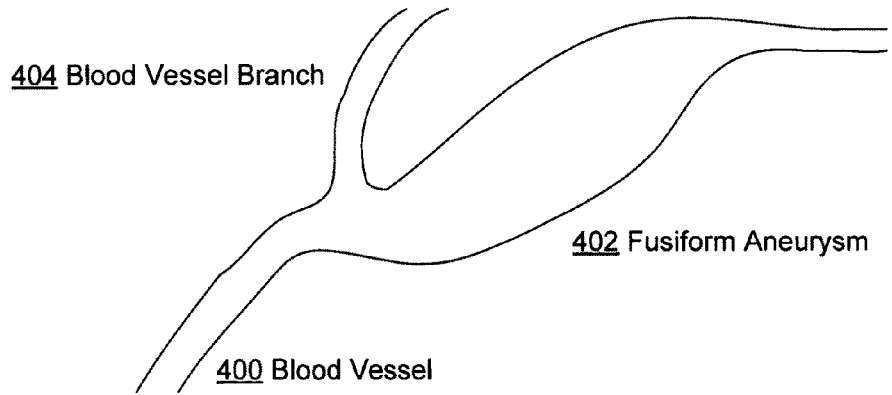
FIG. 4A
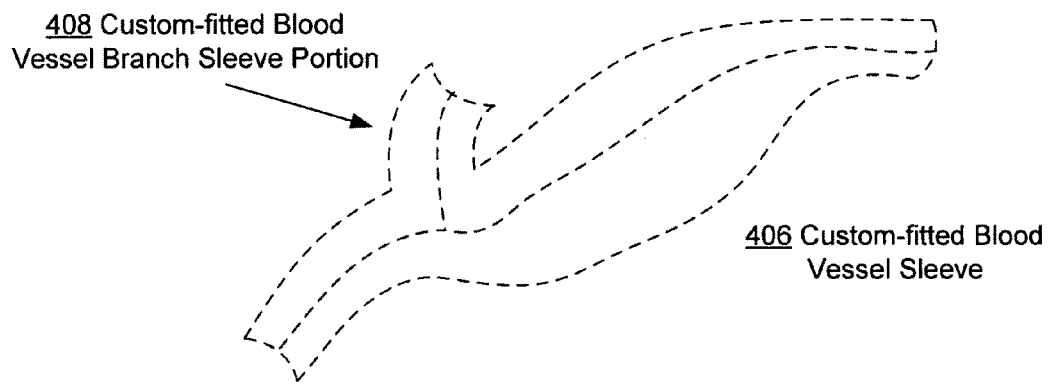
FIG. 4B
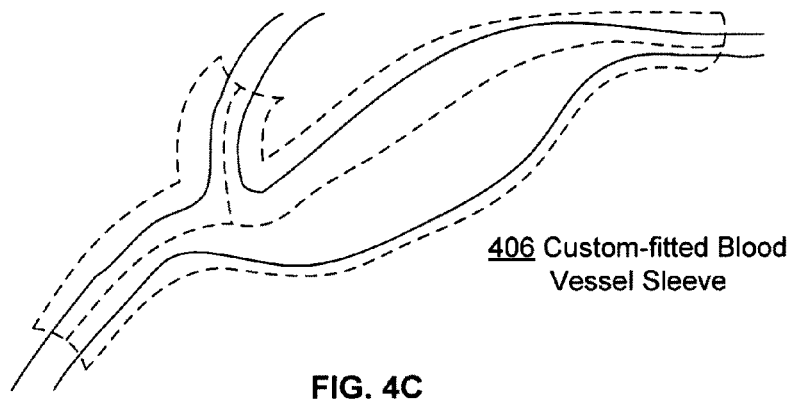
FIG. 4C

FIG. 5
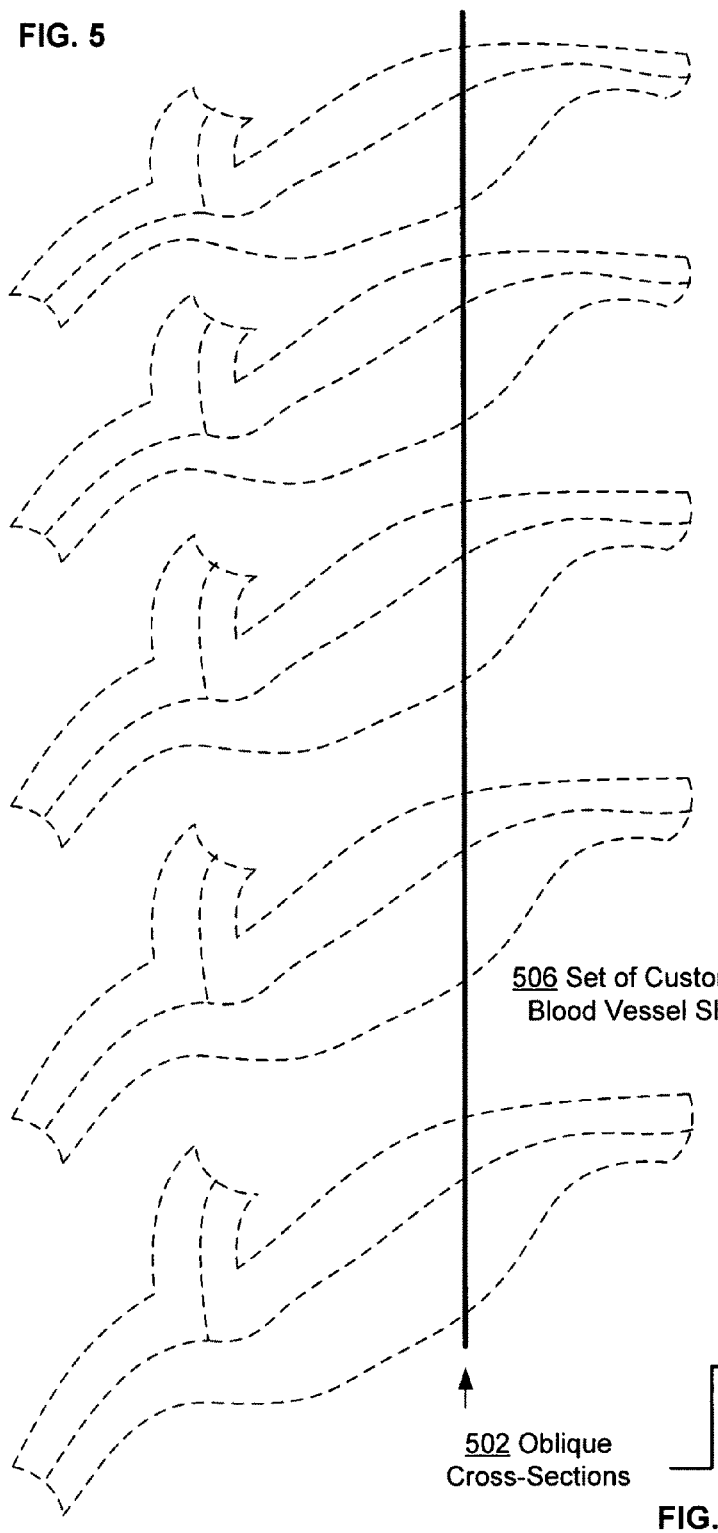
FIG. 5A
FIG. 5B
FIG. 5C
FIG. 5D
506 Set of Custom-fitted Blood Vessel Sleeves
FIG. 5E
502 Oblique Cross-Sections
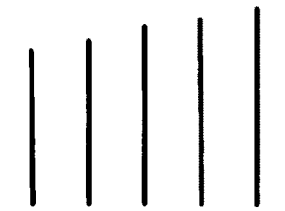
5A 5B 5C 5D 5E
FIG. 5F

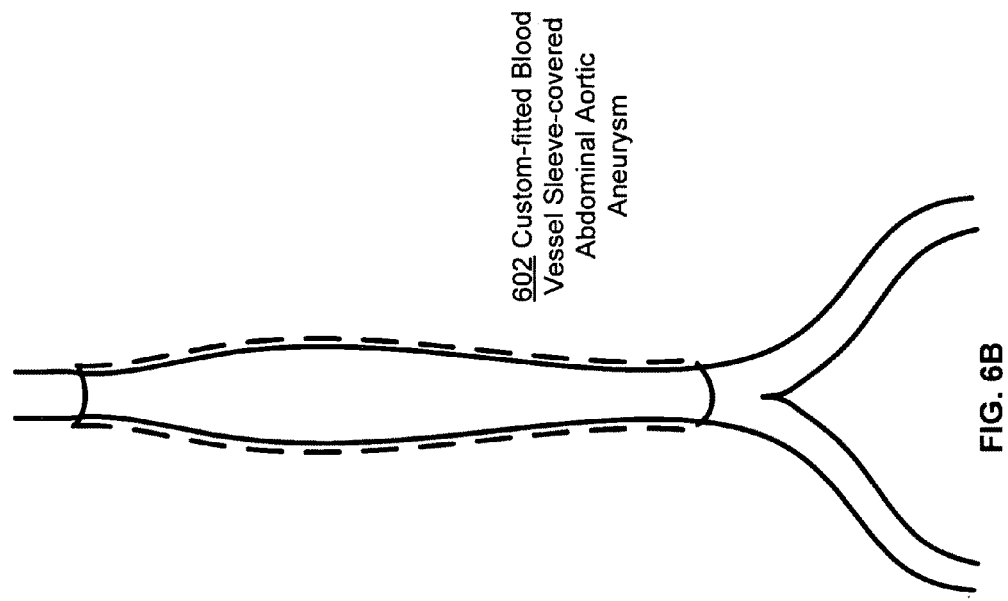
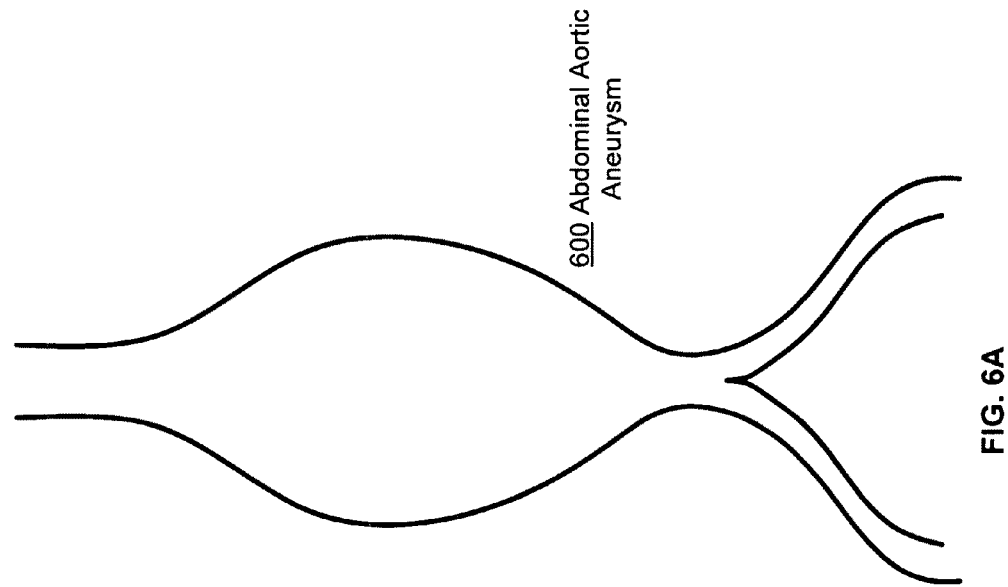

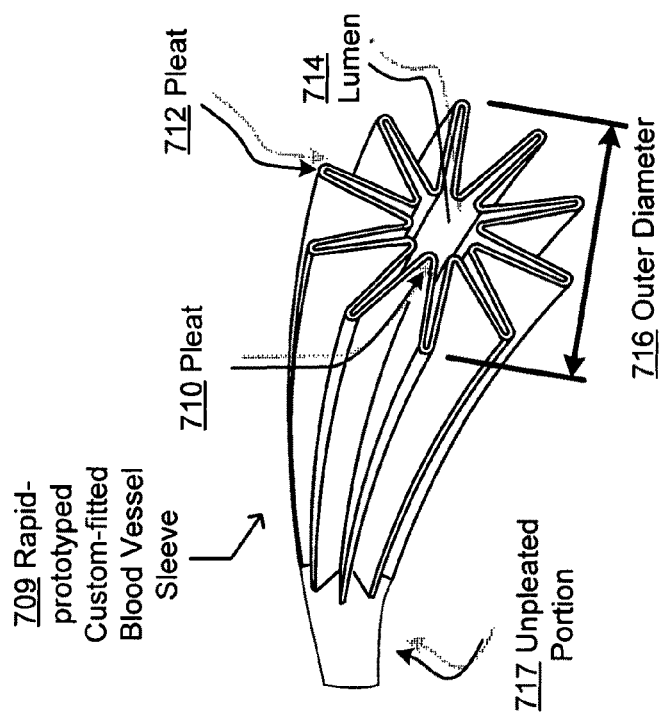
FIG. 7B
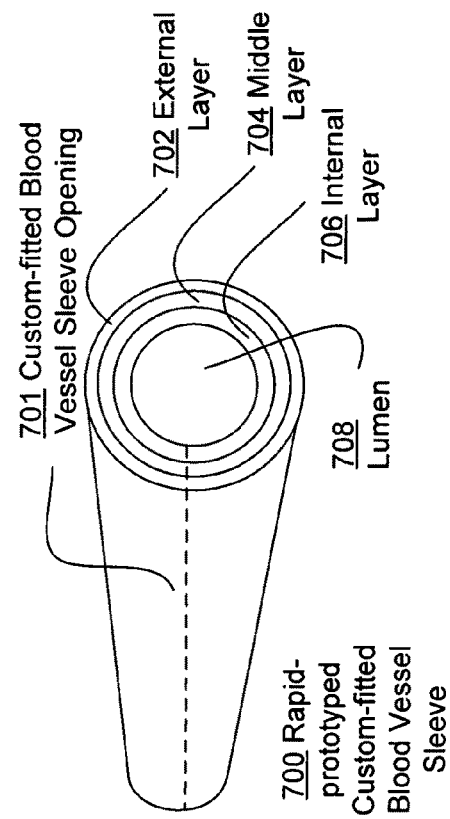
FIG. 7A
FIG. 7

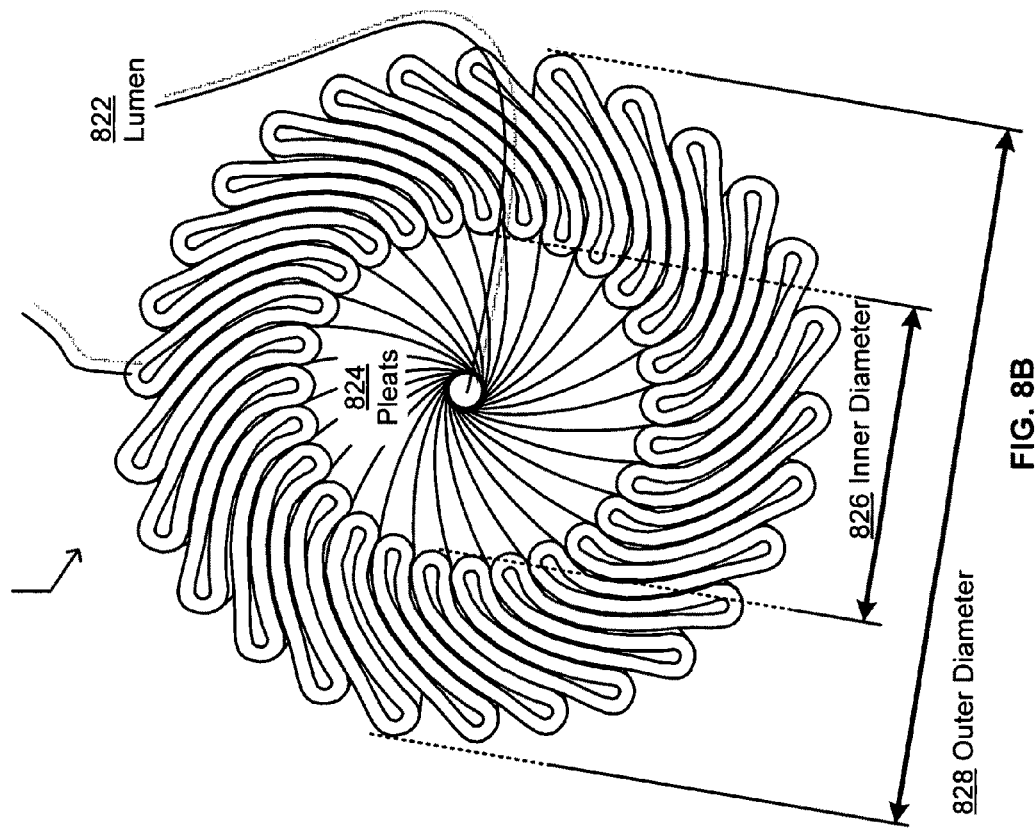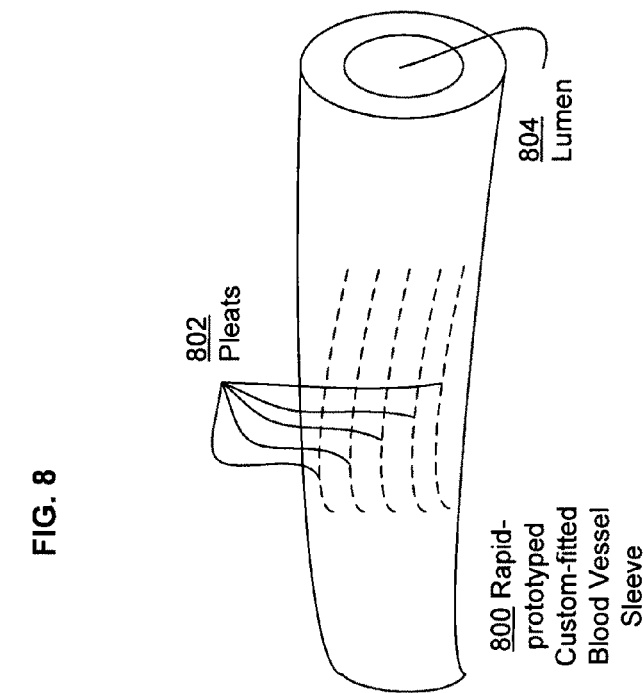
FIG. 8
FIG. 8A
FIG. 8B

RAPID-PROTOTYPED CUSTOM-FITTED BLOOD VESSEL SLEEVE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/454,343, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 16 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/455,010, entitled STENT CUSTOMIZATION SYSTEM AND METHOD, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 16 Jun. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/526,089, entitled STENT CUSTOMIZATION SYSTEM AND METHOD, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 22 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/526,144, entitled STENT CUSTOMIZATION SYSTEM AND METHOD, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 22 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/526,201, entitled STENT CUSTOMIZATION SYSTEM AND METHOD, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 22 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/526,203, entitled STENT CUSTOMIZATION SYSTEM AND METHOD, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 22 Sep. 2006, now U.S. Pat. No. 7,769,603 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/541,377, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 29 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/541,378, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 29 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/541,448, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 29 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/541,452, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 29 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/541,492, entitled SPECIALTY STENTS WITH FLOW CONTROL FEATURES OR THE LIKE, naming Edward K. Y. Jung, Robert Langer, Eric C. Leuthardt, Royce A. Levien, Robert W. Lord, Mark A. Malamud, John D. Rinaldo, Jr., Clarence T. Tegreene and Lowell L. Wood, Jr. as inventors, filed 29 Sep. 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/879,751, entitled CUSTOM-FITTED BLOOD VESSEL SLEEVE, naming Edward S. Boyden, Ralph G. Dacey, Jr., Colin P. Derdeyn, Joshua L. Dowling, Roderick A. Hyde, Muriel Y. Ishikawa, Eric C. Leuthardt, Nathan P. Myhrvold, Clarence T. Tegreene, Lowell L. Wood, Jr., Victoria Y. H. Wood, and Gregory J. Zipfel as inventors, filed 17 Jul. 2007, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, Applicant entity understands that the USPTO's computer programs have certain data entry requirements, and hence Applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

This description relates to blood vessel sleeves.

SUMMARY

An embodiment provides a blood vessel sleeve. In one implementation, the blood vessel sleeve includes but is not limited to a rapid-prototyped blood vessel sleeve that is custom-fitted for a blood vessel at least partly based on anatomical blood vessel data from an individual. In addition to the foregoing, other aspects are described in the claims, drawings, and text forming a part of the present disclosure.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE DRAWINGS

With reference now to FIG. 1, shown is an example of an environment in which one or more blood vessel sleeve technologies may be implemented.

With reference now to FIG. 3, shown are examples of embodiments of blood vessel sleeves, which may serve as a context for introducing one or more devices described herein.

With reference now to FIG. 4, shown are examples of embodiments of blood vessel sleeves, which may serve as a context for introducing one or more devices described herein.

With reference now to FIG. 5, shown are examples of embodiments of blood vessel sleeves, which may serve as a context for introducing one or more devices described herein.

With reference now to FIG. 6, shown are examples of embodiments of blood vessel sleeves, which may serve as a context for introducing one or more devices described herein.

With reference now to FIG. 7, shown are examples of embodiments of blood vessel sleeves, which may serve as a context for introducing one or more devices described herein.

With reference now to FIG. 8, shown are examples of embodiments of blood vessel sleeves, which may serve as a context for introducing one or more devices described herein.

Figure 9:
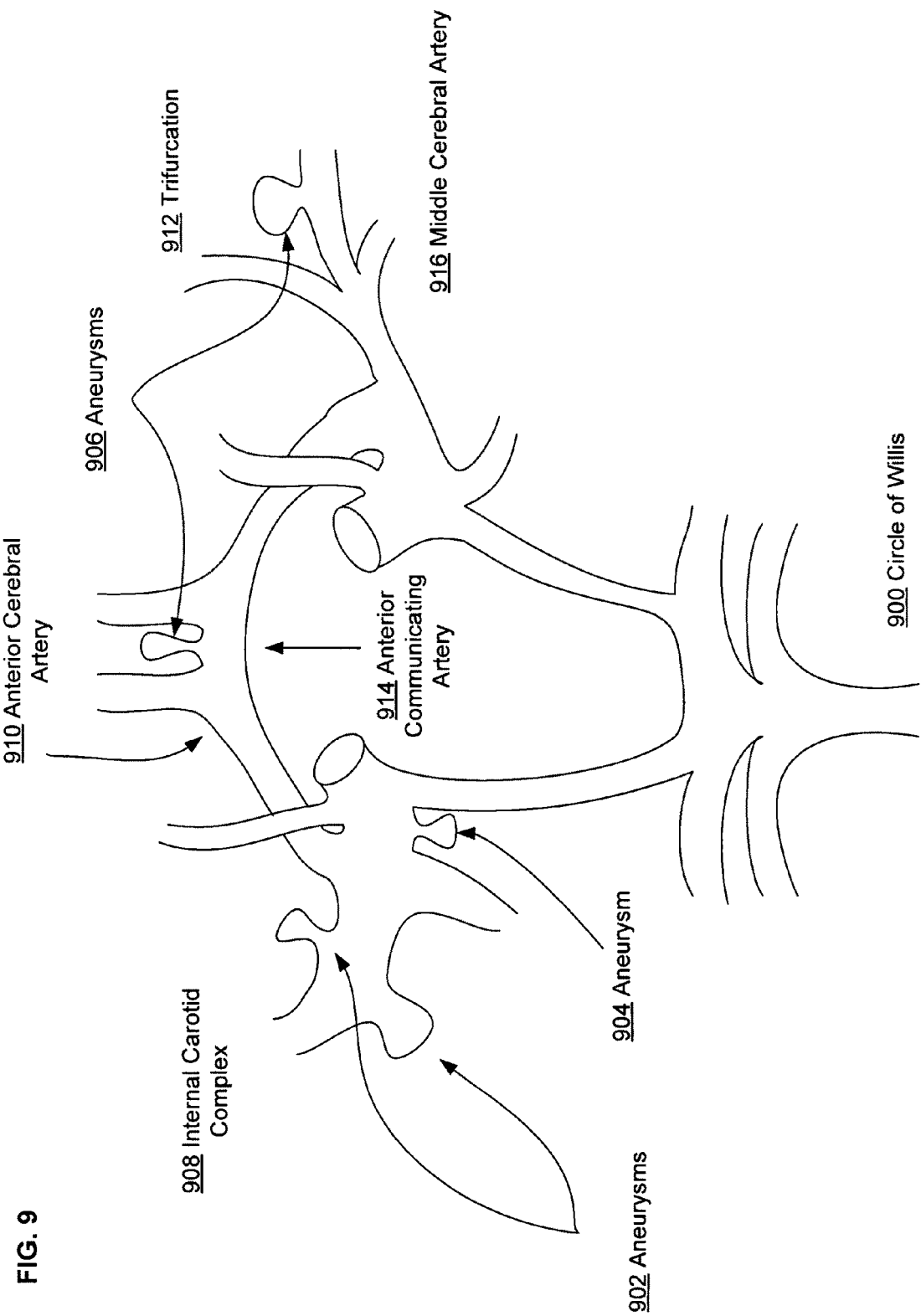

With reference now to FIG. 9, shown are examples of blood vessel anatomy, which may serve as a context for introducing one or more devices described herein.

Figure 10:
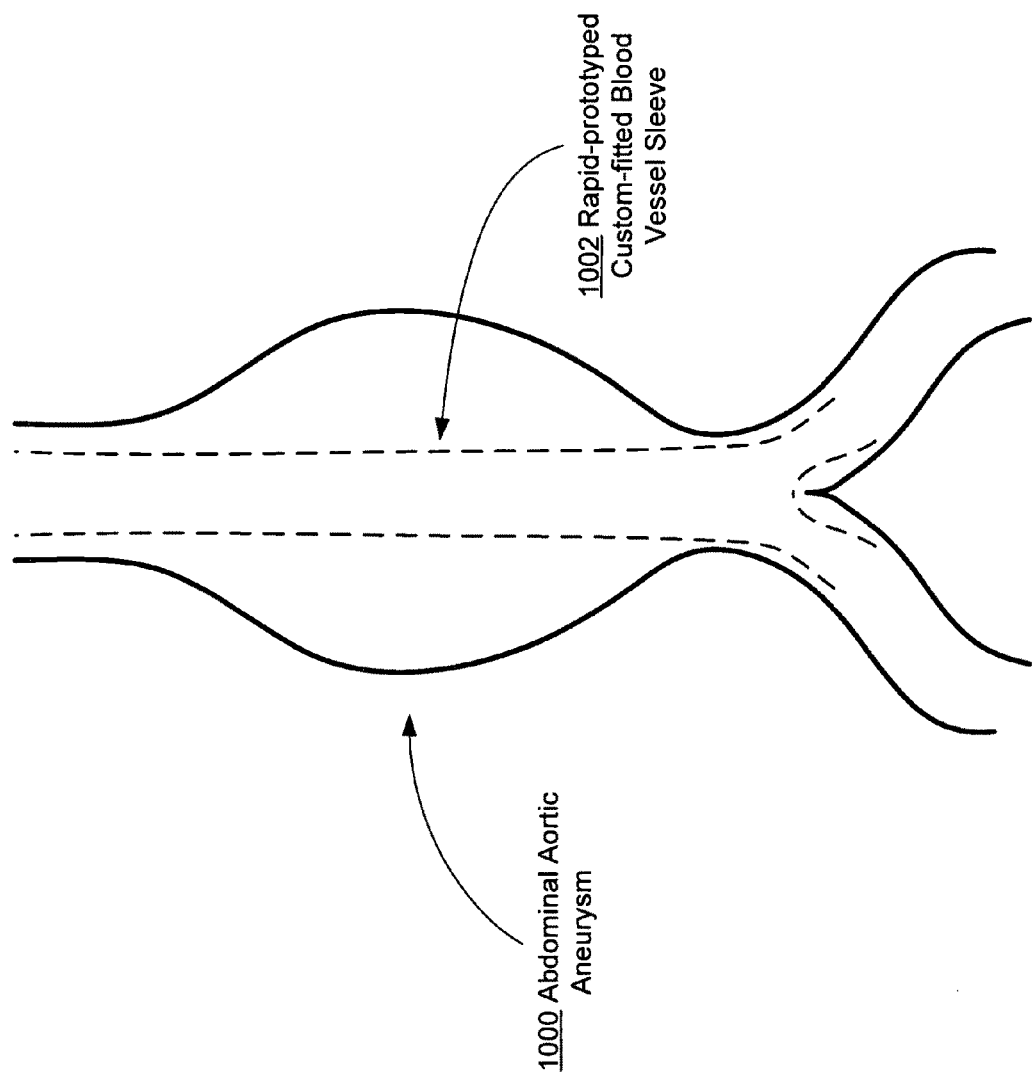

With reference now to FIG. 10, shown are examples of embodiments of blood vessel sleeves, which may serve as a context for introducing one or more devices described herein.

Figure 11:
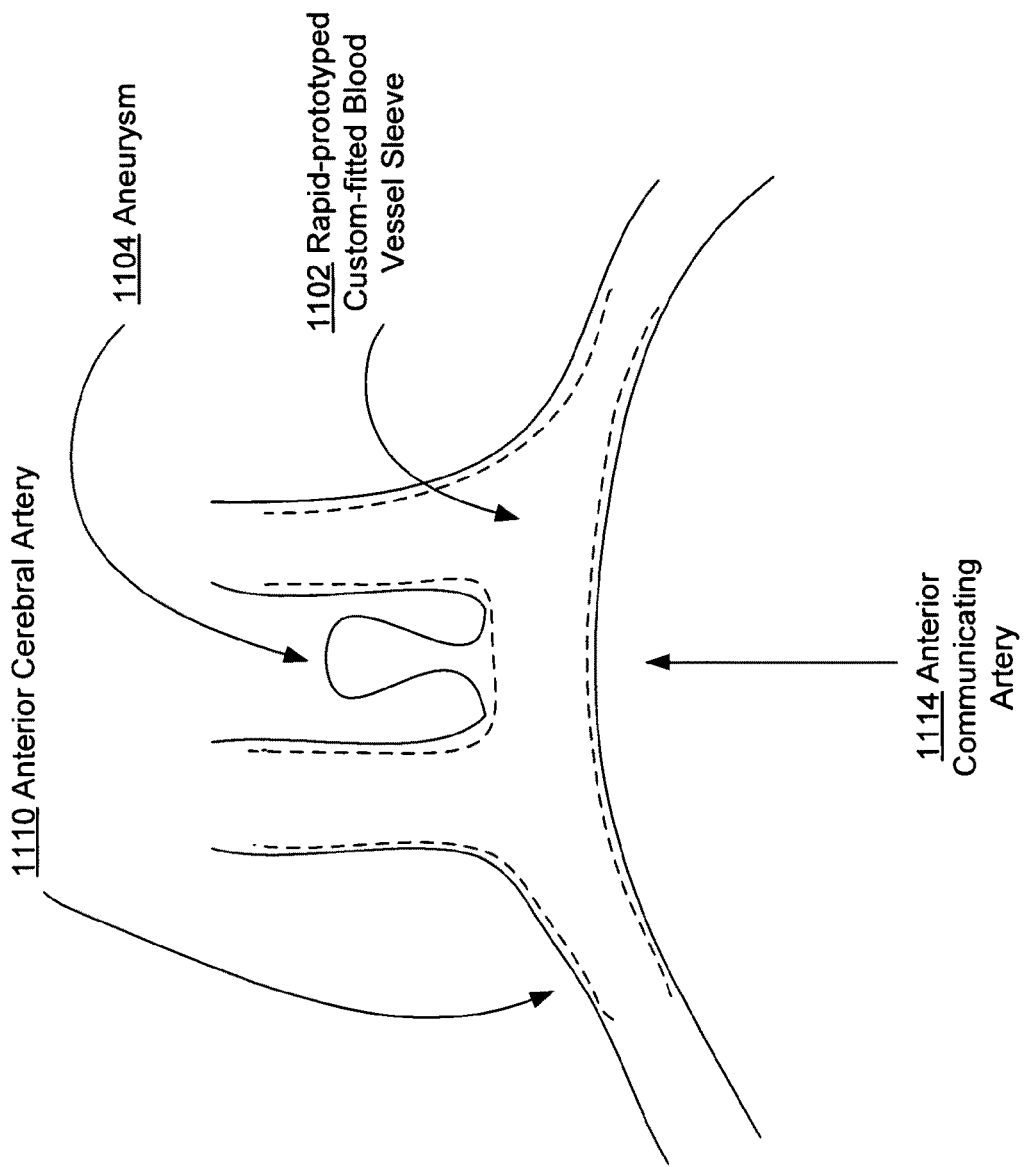

With reference now to FIG. 11, shown are examples of embodiments of blood vessel sleeves, which may serve as a context for introducing one or more devices described herein.

The use of the same symbols in different drawings typically indicates similar or identical items.

DETAILED DESCRIPTION

Figure 1:
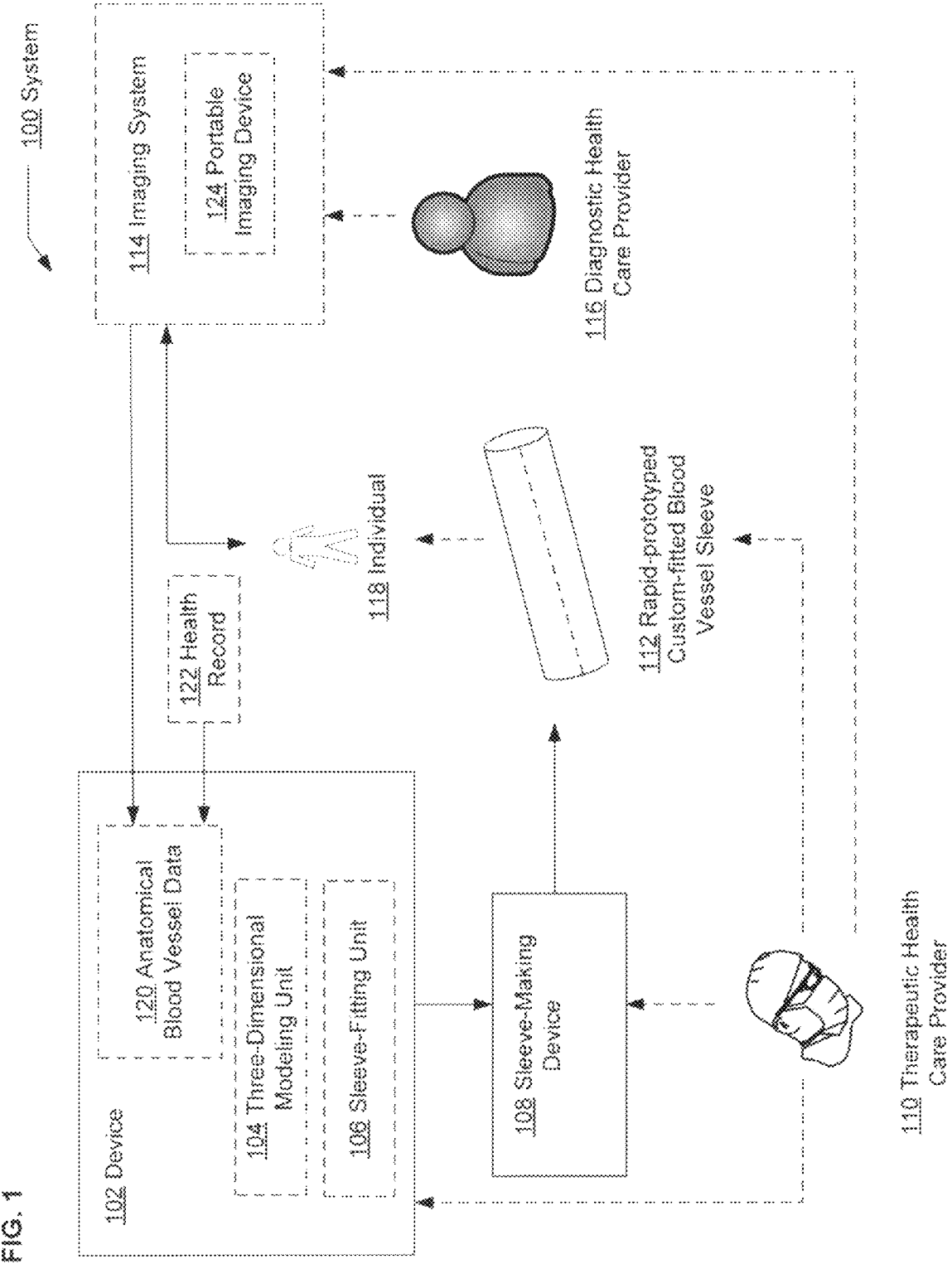

FIG. 1 illustrates an example system 100 in which embodiments may be implemented. The system 100 includes at least one device 102. The at least one device 102 may contain, for example, a three-dimensional modeling unit 104 and a sleeve-fitting unit 106. Imaging system 114 may generate anatomical blood vessel data 120 from an individual 118, or anatomical blood vessel data 120 from an individual 118 may be obtained from a health record 122 that is external to the device 102. Imaging system 114 may be operated by diagnostic health care provider 116 and/or therapeutic health care provider 110 to obtain anatomical blood vessel data 120 from an individual 118.

Therapeutic health care provider 110 may interact with the device 102 to determine blood vessel sleeve specifications based on anatomical blood vessel data 120 from an individual 118. Therapeutic health care provider 110 may also interact with sleeve-making device 108 to obtain a rapid-prototyped custom-fitted blood vessel sleeve 112 based on anatomical blood vessel data 120 from an individual 118. Therapeutic health care provider 110 may then employ the rapid-prototyped custom-fitted blood vessel sleeve 112 to address a blood vessel of individual 118 in an open surgical procedure, in a laparoscopic surgery procedure, through a catheter insertion procedure, or the like.

In some embodiments, the imaging system 114 and the device 102 may be combined in a single device, or the imaging system 114, the device 102, and the sleeve-making device 108 may be combined in a single device. In some embodiments the imaging system 114 may be a portable imaging device 124 that can communicate with the at least one device 102, on which the sleeve-fitting unit 106 is operable, via a wireless network for example. In some embodiments, the sleeve-making device 108 may be operable remotely through the device 102 via, for example, a network connection.

In FIG. 1, the at least one device 102 is illustrated as possibly being included within a system 100. Any kind of computing device may be used in connection with the three-dimensional modeling unit 104 and/or sleeve-fitting unit 106, such as, for example, a workstation, a desktop computer, a mobile computer, a networked computer, a collection of servers and/or databases, cellular phone, personal entertainment device, or a tablet PC.

Additionally, not all of the three-dimensional modeling unit 104 and/or sleeve-fitting unit 106 need be implemented on a single computing device. For example, the three-dimensional modeling unit 104 may be implemented and/or operable on a remote computer, while the sleeve-fitting unit 106 and/or sleeve-making device 108 is implemented and/or stored on a local computer. Further, aspects of the three-dimensional modeling unit 104, sleeve-fitting unit 106, imaging system 114, and/or sleeve-making device 108 may be implemented in different combinations and implementations than that shown in FIG. 1. For example, functionality of the sleeve-making device 108 may be incorporated into the device 102. In some embodiments, the at least one device 102 may process anatomical blood vessel data 120 from an individual 118 according to anatomical profiles available as updates through a health records network.

The anatomical blood vessel data 120 from an individual 118 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
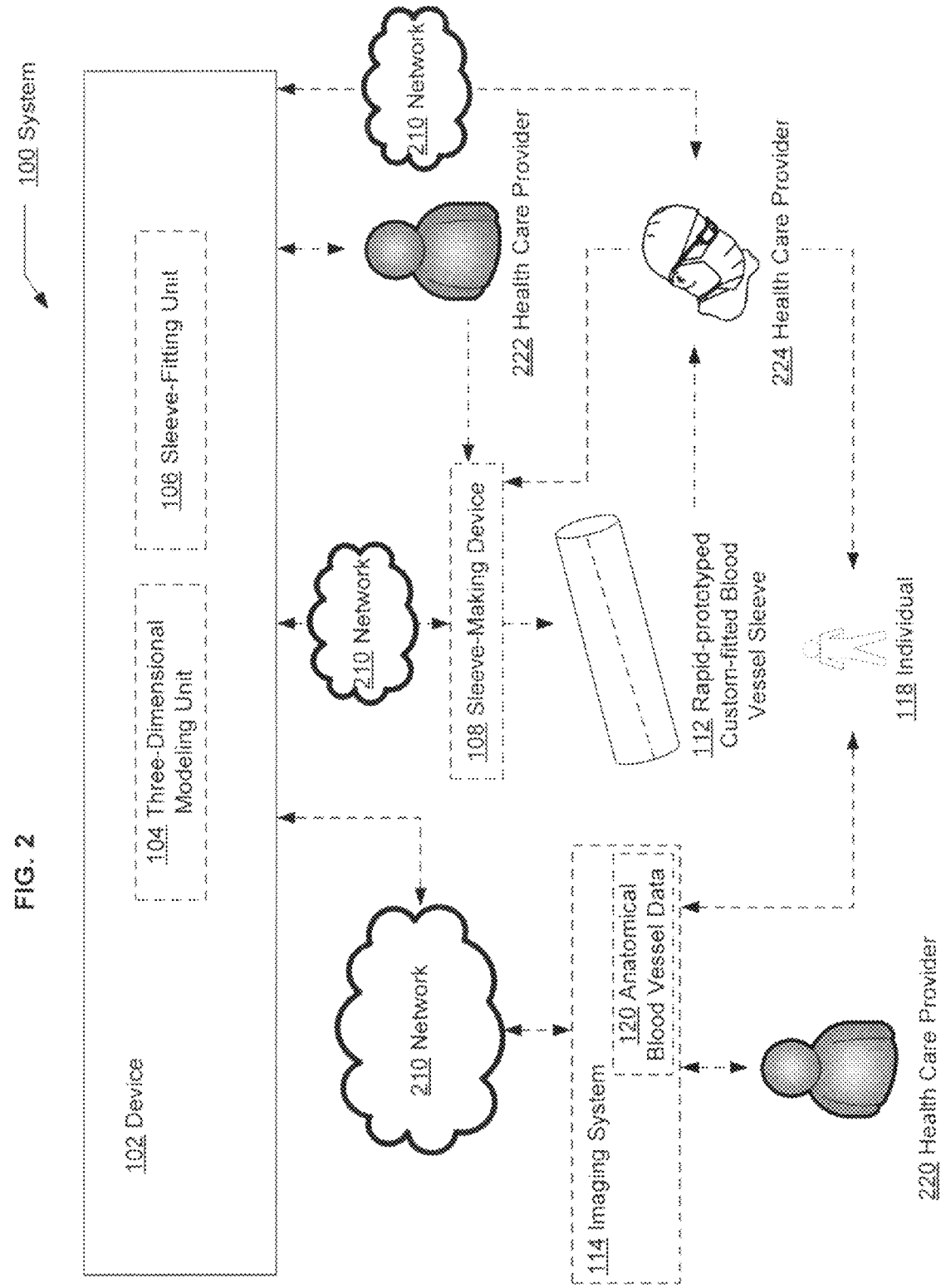
FIG. 2 illustrates certain alternative embodiments of the exemplary environment of FIG. 1.

FIG. 2 illustrates certain alternative embodiments of the system 100 of FIG. 1. In FIG. 2, a health care provider 220 may interact with imaging system 114 to obtain anatomical blood vessel data 120 from an individual 118. The anatomical blood vessel data 120 from an individual 118 may be sent through a network 210 to three-dimensional modeling unit 104 and/or sleeve-fitting unit 106 operable on at least one device 102. The three-dimensional modeling unit 104 and/or sleeve-fitting unit 106 may be implemented on the at least one device 102, or elsewhere within the system 100 but separate from the at least one device 102. The at least one device 102 may be in communication remotely over a network 210 or locally with the sleeve-making device 108, health care provider 222, and/or health care provider 224. A health care provider may interact with the at least one device 102, three-dimensional modeling unit 104, sleeve-fitting unit 106, and/or sleeve-making device 108 through, for example, a user interface. Of course, it should be understood that there may be other health care providers other than the specifically-illustrated health care provider 220, health care provider 222, and/or health care provider 224, for example, each with access to at least a portion of system 100.

In this way, the sleeve-making device 108 may generate a rapid-prototyped custom-fitted blood vessel sleeve 112, perhaps remotely via a network 210 as if the health care provider 220, health care provider 222, and/or health care provider 224 were interacting locally with the at least one device 102 and/or sleeve-making device 108.

As referenced herein, the at least one device 102, three-dimensional modeling unit 104, and/or sleeve-fitting unit 106 may be used to perform various data querying, recall, and/or manipulation techniques with respect to the anatomical blood vessel data 120, in order to, for example, construct a model of a portion of a blood vessel or determine specifications of a blood vessel sleeve for use in treating a portion of a blood vessel. For example, where the anatomical blood vessel data 120 is organized, keyed to, and/or otherwise accessible using one or more reference health condition attributes or profiles, various Boolean, statistical, and/or semi-boolean searching techniques may be performed to match anatomical blood vessel data 120 with reference health data, attributes, or profiles.

Many examples of databases and database structures may be used in connection with the at least one device 102, three-dimensional modeling unit 104, and/or sleeve-fitting unit 106. Such examples include hierarchical models (in which data is organized in a tree and/or parent-child node structure), network models (based on set theory, and in which multi-parent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

For example, SQL or SQL-like operations over one or more of reference blood vessel attribute may be performed, or Boolean operations using a reference health attribute may be performed. For example, weighted Boolean operations may be performed in which different weights or priorities are assigned to one or more of the reference health attributes, perhaps relative to one another. For example, a number-weighted, exclusive-OR operation may be performed to request specific weightings of desired (or undesired) anatomical blood vessel data 120 to be included or excluded.

FIG. 3 illustrates an exemplary embodiment related to a custom-fitted blood vessel sleeve. In FIG. 3 and in following figures that include various examples of custom-fitted blood vessel sleeves, discussion and explanation may be provided with respect to the above-described system environments of FIGS. 1-2, and/or with respect to other examples and contexts. However, it should be understood that the exemplary embodiments may be executed in a number of other environments and contexts, and/or in modified versions of FIGS. 1-9. Also, although the various exemplary embodiments are presented in the context of the system environments of FIGS. 1-2, it should be understood that the various exemplary embodiments may be produced by other systems than those which are illustrated.

With respect to FIG. 3A, blood vessel 300 from an individual 118 is shown, the blood vessel 300 having a portion bearing a berry aneurysm 302. With respect to FIG. 3B, shown is a rapid-prototyped blood vessel sleeve that is custom-fitted for a blood vessel at least partly based on anatomical blood vessel data from an individual 118. For example, shown is custom-fitted blood vessel sleeve 306 that may be placed around the blood vessel 300 to support and/or confine the berry aneurysm 302. FIG. 3B thus shows a rapid-prototyped blood vessel sleeve that is custom-fitted for at least one aneurysm on at least one blood vessel at least partly based on anatomical blood vessel data from the individual 118. Aneurysms may involve arteries or veins and have various causes. They are commonly further classified by shape, structure, and location. A saccular aneurysm may resemble a small bubble that appears on the side of a blood vessel. The innermost layer of an artery, in direct contact with the flowing blood, is the tunica intima, commonly called the intima. Adjacent to this layer is the tunica media, known as the media and composed of smooth muscle cells and elastic tissue. The outermost layer is the tunica adventitia or tunica externa. This layer is composed of tougher connective tissue. A saccular aneurysm develops when fibers in the outer layer separate allowing the pressure of the blood to force the two inner layers to balloon through. A saccular aneurysm with a narrow neck connecting the bubble-like pouch to the main blood vessel is known as a berry aneurysm.

A fusiform aneurysm may be a bulging around the entire circumference of the vessel without protrusion of the inner layers. It may be shaped like a football or spindle.

Aneurysms can result from hypertension in conjunction with atherosclerosis that weakens the tunica adventitia, from congenital weakness of the adventitial layer (as in Marfan syndrome), and/or from infection.

Rupture and blood clotting are two health risks involved with aneurysms. Rupture typically leads to a drop in blood pressure, rapid heart rate, and/or lightheadedness. The risk of death is high except for the case of rupture of blood vessels in the extremities. Risk factors for an aneurysm are diabetes, obesity, hypertension, tobacco smoking, and alcoholism.

Also known as intracranial aneurysm or brain aneurysm, cerebral aneurysms make up a large proportion of aneurysm incidence. A common location of cerebral aneurysms is on the arteries at the base of the brain, known as the Circle of Willis. Approximately 85% of cerebral aneurysms develop in the anterior part of the Circle of Willis, and involve the internal carotid arteries and their major branches that supply the anterior and middle sections of the brain. The most common sites include the anterior communicating artery (30-35%), the bifurcation of the internal carotid and posterior communicating artery (30-35%), the bifurcation of the middle cerebral artery (20%), the bifurcation of the basilar artery, and the remaining posterior circulation arteries (5%). The custom-fitted blood vessel sleeve 306 may accordingly be a rapid-prototyped blood vessel sleeve that is custom-fitted for at least one cerebral artery at least partly based on anatomical cerebral artery data from the individual 118 (see FIG. 9).

Eventual rupture of a cerebral aneurysm may be called an aneurysmal subarachnoid hemorrhage, in which blood flows into the subarachnoid space of the brain and forms clots. One complication of aneurysmal subarachnoid hemorrhage is the development of vasospasm. Approximately 1 to 2 weeks following the initial hemorrhage, an individual 118 may experience spasm of the cerebral arteries, which may result in stroke. The etiology of vasospasm is thought to be secondary to an inflammatory process that occurs as the blood in the subarachnoid space is resorbed.

Vasospasm may be monitored in a variety of ways. Non-invasive methods include transcranial Doppler, which is a method of measuring the velocity of blood in the cerebral arteries using ultrasound. As the vessels narrow due to vasospasm, the velocity of blood increases. The amount of blood reaching the brain can also be measured by computed tomography scanning (CT scanning), magnetic resonance imaging (MRI), or nuclear perfusion scanning.

Non-intracranial aneurysms commonly arise distal to the origin of the renal arteries at the infrarenal abdominal aorta, a condition often caused by atherosclerosis. The thoracic aorta may also be involved. One common form of thoracic aortic aneurysm involves widening of the proximal aorta and the aortic root, leading to aortic insufficiency. Common aortic aneurysms may include abdominal aortic aneurysm and aneurysm of the aortic arch.

The human aorta is a relatively low-resistance circuit for circulating blood. The lower extremities have higher arterial resistance, and the repeated trauma of a reflected arterial wave on the distal aorta may injure a weakened aortic wall and contribute to aneurysmal degeneration. Systemic hypertension compounds the injury, accelerates the expansion of known aneurysms, and may contribute to their formation. The custom-fitted blood vessel sleeve 306 may accordingly be a rapid-prototyped blood vessel sleeve that is custom-fitted for at least one aorta at least partly based on anatomical aorta data from the individual 118.

Aneurysms occur in the legs also, particularly in the deep vessels (e.g., the popliteal vessels in the knee). Arterial aneurysms are much more common, but venous aneurysms also occur (e.g., the popliteal venous aneurysm). Blood clots from popliteal arterial aneurysms can travel downstream and suffocate tissue. Only if the resulting pain and/or numbness are ignored over a significant period of time will such extreme results as amputation be needed. Clotting in popliteal venous aneurysms are much more serious as the clot can embolize and travel to the heart, or through the heart to the lungs (i.e., a pulmonary embolism).

The occurrence and expansion of an aneurysm in a given segment of the arterial tree involves local hemodynamic factors and factors intrinsic to the arterial segment itself. Hemodynamically, the coupling of aneurysmal dilation and increased wall stress is approximated by the Law of Laplace. Specifically, the Law of Laplace states that the (arterial) wall tension is proportional to the pressure times the radius of the arterial conduit ($T = P \times R$). As diameter increases, wall tension increases, which contributes to increasing diameter. As tension increases, risk of rupture increases. Increased pressure (systemic hypertension) and increased aneurysm size aggravate wall tension and therefore increase the risk of rupture. In addition, the vessel wall is supplied by the blood within its lumen in humans. Therefore in a developing aneurysm, the most ischemic portion of the aneurysm is at the farthest end, resulting in weakening of the vessel wall there and aiding further expansion of the aneurysm. Thus all aneurysms will eventually, if left to complete their evolution, rupture without intervention.

Treatment of cerebral aneurysm may include surgical intervention (i.e., invasive surgery) called clipping, in which a craniotomy is performed, followed by placement of a titanium clip around the aneurysm neck. Another treatment method, coil embolization, involves the insertion of a catheter through the groin with a small microcatheter navigated to the aneurysm itself through the cerebral arteries. Coils known as Guglielmi Detachable Coils (GDCs) are then deployed into the aneurysm, filling it from within and thus preventing blood from entering the aneurysm itself by forming a large clot on the coils.

For aortic aneurysms or aneurysms that happen in the vessels that supply blood to the arms, legs, and head, surgery may involve inserting a covered metallic stent graft through the arteries of the leg to be deployed across the inside of the weakened section of the blood vessel.

A false or pseudoaneurysm does not primarily involve distortion of a blood vessel, but instead is composed of a collection of blood leaking out of an artery or vein into a region next to the blood vessel and confined by the surrounding tissue. This blood-filled cavity may eventually either clot enough to seal the leak or it may rupture the tissue enclosing it and disperse into nearby tissues. Pseudoaneurysms may be caused by trauma that punctures the artery, and are a known complication of percutaneous arterial procedures such as arteriography, arterial grafting, or use of an artery for injection, such as by drug abusers repeatedly searching with a needle for a usable vein. Like true aneurysms, pseudoaneurysms may be felt as an abnormal pulsatile mass on palpation.

In FIG. 3B, the custom-fitted blood vessel sleeve 306 is shown with a custom-fitted blood vessel sleeve aperture 314 that may accommodate a blood vessel branch 304 associated with blood vessel 300. The custom-fitted blood vessel sleeve 306 further can have dimensions that accommodate a berry aneurysm 302 or other aneurysm. Appropriate dimensions for the custom-fitted blood vessel sleeve 306 may be obtained by the device 102, imaging system 114, and/or sleeve-fitting unit 106 operable on the device 102 or otherwise associated with system 100. Alternatively, specifications for the custom-fitted blood vessel sleeve 306 may be obtained via an integrated system containing imaging system 114, three-dimensional modeling unit 104, sleeve-fitting unit 106, and sleeve-making device 108. Accordingly, a custom-fitted blood vessel sleeve 306 may accommodate various blood vessel dimensions and features, including blood vessel diameter, blood vessel branching, blood vessel curvature 308, aneurysm dimensions, or other anatomical variation in an individual 118.

In order to be placed on a blood vessel, the custom-fitted blood vessel sleeve 306 may include a custom-fitted blood vessel sleeve opening 312, by which the custom-fitted blood vessel sleeve 306 may be passed over a longitudinal axis of the blood vessel 300, for example, and any blood vessel branch 304 that may be present. The custom-fitted blood vessel sleeve 306 may also include at least one closure means, as discussed below, such that after passing over the longitudinal axis of the blood vessel 300, the sleeve may be closed to resume, for example, a closed cylinder configuration.

With respect to FIG. 3C, shown is the custom-fitted blood vessel sleeve 306 in place around blood vessel 300 and berry aneurysm 302. In the case of an aneurysm, for example, that is in proximity to a blood vessel branch 304, the custom-fitted blood vessel sleeve 306 may incorporate a custom-fitted blood vessel sleeve aperture 314 through which the blood vessel branch 304 may pass, as shown in FIG. 3C.

Placement of custom-fitted blood vessel sleeve 306 on an aneurysm-affected portion of a blood vessel 300 may serve to inhibit, prevent, and/or mitigate rupture of the aneurysm-affected portion of the blood vessel 300. Further, the custom-fitted blood vessel sleeve 306 may be designed with specifications such that when the custom-fitted blood vessel sleeve 306 is placed on the blood vessel 300, the aneurysm is compressed in diameter and thereby supported, for example, circumferentially by the custom-fitted blood vessel sleeve 306. In this scenario, the circumference of the aneurysm-affected portion of the blood vessel 300 may be reduced, with an attendant reduction in blood vessel wall tension according to the Law of Laplace, as discussed above.

Such reduction in wall tension afforded by a custom-fitted blood vessel sleeve 306 may address an aneurysm-affected portion of a blood vessel 300, an atherosclerosis-affected portion of a blood vessel 300, and/or other condition involving compromised blood vessel wall integrity.

FIG. 4 illustrates an exemplary embodiment related to a custom-fitted blood vessel sleeve. With respect to FIG. 4A, blood vessel 400 from an individual 118 is shown, the blood vessel 400 having a fusiform aneurysm 402 and a blood vessel branch 404.

With respect to FIG. 4B, shown is a custom-fitted blood vessel sleeve 406 that is based on anatomical blood vessel data 120 from an individual 118. In this example, the custom-fitted blood vessel sleeve 406 may include an integrated custom-fitted blood vessel branch sleeve portion 408 that may be placed around a portion of the blood vessel branch 404, typically in conjunction with placing the custom-fitted blood vessel sleeve 406 around a portion of blood vessel 400 and/or fusiform aneurysm 402. The custom-fitted blood vessel sleeve 406 may accordingly be a rapid-prototyped blood vessel sleeve that is custom-fitted for at least one branched blood vessel at least partly based on anatomical blood vessel data from the individual 118.

With respect to FIG. 4C, shown is the custom-fitted blood vessel sleeve 406 in place around blood vessel 400, fusiform aneurysm 402, and blood vessel branch 404.

FIG. 5 illustrates an exemplary embodiment related to a custom-fitted blood vessel sleeve. With respect to FIGS. 5A-5E, a set of custom-fitted blood vessel sleeves 506 of varying size is depicted. This size gradation is further depicted in FIG. 5F, wherein oblique cross-sections 502 are presented for each of the custom-fitted blood vessel sleeves of FIGS. 5A-5E. The oblique cross-sections 502 are shown as lines of varying length, beginning with 5A and increasing through 5E, corresponding to cross-sections of FIGS. 5A through 5E, respectively.

FIG. 6 illustrates an exemplary embodiment related to a custom-fitted blood vessel sleeve. With respect to FIG. 6A, an abdominal aortic aneurysm 600 is shown. FIG. 6B depicts a custom-fitted blood vessel sleeve-covered abdominal aortic aneurysm 602. As shown in FIG. 6B, the rapid-prototyped custom-fitted blood vessel sleeve may be of a smaller diameter, for example, than the aneurysm around which it is placed. In effect, placement of a custom-fitted blood vessel sleeve in this way may constrict the blood vessel and return it to a diameter that is closer to or the same as its diameter prior to occurrence of the aneurysm. In this way the custom-fitted blood vessel sleeve may provide support for the blood vessel wall and act to prevent rupture of the aneurysm.

Accordingly, a rapid-prototyped custom-fitted blood vessel sleeve may be a rapid-prototyped blood vessel sleeve that is custom-fitted for the exterior of a blood vessel at least partly based on anatomical blood vessel data from the individual. Alternatively, a rapid-prototyped custom-fitted blood vessel sleeve may be a rapid-prototyped blood vessel sleeve that is custom-fitted for the interior of a blood vessel at least partly based on anatomical blood vessel data from the individual. Such a sleeve fitted to the interior of a blood vessel is shown in FIG. 10 and FIG. 11.

FIG. 7 illustrates an exemplary embodiment related to a custom-fitted blood vessel sleeve. With respect to FIG. 7A, an oblique view of a cross-section of a rapid-prototyped custom-fitted blood vessel sleeve 700 is shown. The rapid-prototyped custom-fitted blood vessel sleeve 700 may be composed of single or multiple layers to confer desired properties of stiffness, applicability to a blood vessel 300, expansion or contraction capability, durability, ease of manufacture, drug delivery capability, or the like. The rapid-prototyped custom-fitted blood vessel sleeve 700 may accordingly be a rapid-prototyped, multiple-layered blood vessel sleeve that is custom-fitted for the blood vessel at least partly based on anatomical blood vessel data from the individual 118. As used herein, the word "multiple" refers to "at least two or more." FIG. 7A shows a rapid-prototyped custom-fitted blood vessel sleeve 700 having a lumen 708, a custom-fitted blood vessel sleeve opening 701, an external layer 702, a middle layer 704, and an internal layer 706. In some embodiments, the custom-fitted blood vessel sleeve opening 701 may consist of a perforation that allows a therapeutic health care provider 110, for example, to open the rapid-prototyped custom-fitted blood vessel sleeve 700 immediately prior to placement on a blood vessel. Alternatively, no opening or perforation may be present, and a therapeutic health care provider 110 may cut the rapid-prototyped custom-fitted blood vessel sleeve 700 to create an opening for placement over a blood vessel.

In another embodiment, the rapid-prototyped custom-fitted blood vessel sleeve 700 may be a substantially transparent rapid-prototyped blood vessel sleeve that is custom-fitted for at least one blood vessel at least partly based on anatomical blood vessel data from the individual 118. In this embodiment, the transparent nature of the blood vessel sleeve may allow a surgeon or other therapeutic health care provider 110 to visually examine the fit of the blood vessel sleeve more closely, and also to visually examine the status of the blood vessel sleeve and blood vessel at various times after the initial placement, if necessary. Such a substantially transparent sleeve may be particularly useful in cases where a problem has developed in the area of the sleeve, such as hemorrhaging, embolism, and/or stenosis of the blood vessel.

The rapid-prototyped custom-fitted blood vessel sleeve 700 may be manufactured from many kinds of materials appropriate for use in the human body, known to those of skill in the art. For example, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve at least partly made of a biocompatible material. Biocompatible material may include, for example, a polymer, a metal and/or metal alloy, a ceramic, a natural material, a pyrolytic carbon material, and/or composites thereof, or the like. Biocompatible material may also include biomimetic material and/or material with surface functionalization via protein deposition or self-assembling peptide scaffold deposition. Additionally, methods known in the art to render biocompatible chemically inert or reactive surfaces may be used, including, for example, plasma processing and/or the use of polyanhydrides. Another method for detoxification of solid freeform fabrication materials is found in U.S. Pat. No. 6,996,245 B2 entitled "Detoxification of solid freeform fabrication materials." This process involves chemical extraction and has been used to detoxify, for example, a custom hearing aid shell produced by stereolithography from an acrylate photopolymer resin.

Polyvinyl chloride is one commonly used polymer in medical devices, and other biocompatible polymers commonly used are silicone, polyurethane, polycarbonates, polyester and polyethylene, biodegradable polymers, bioactive polymers, hydrogels, molecular imprinted polymers, conductive polymers, and biopolymers. Such polymers may be applied to meshes, foams, sponges or hydrogels, for example, to form a rapid-prototyped custom-fitted blood vessel sleeve 700. Bioactive polymers may serve secondary functions such as stimulating or inhibiting tissue growth, and/or promoting adhesion.

Titanium, stainless steel, and chromium steel are examples of metals used in medical implants. Metal alloys are also commonly used to obtain desired strength, malleability, and/or fabrication properties. Composites comprised of artificial growth factors, natural materials, carbon fibers, and/or polymers are also useful as biocompatible material.

Biocompatible nanomaterial may also be used. Some such materials known to those of skill in the art may provide rejection-resistant implants. Tissue engineering using polymer scaffolds for cell hosting may also provide a biocompatible material for use with a rapid-prototyped custom-fitted blood vessel sleeve 700.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve having at least one of a substantially polymer composition, a substantially plastic composition, a substantially thermoplastic composition, a substantially photopolymer composition, or a substantially elastomeric composition.

In some embodiments, an internal layer 706 may comprise a surface that is suitable for contact with the collagen and smooth muscle cells of the tunica adventitia (i.e., the outer layer of the blood vessel) or the tunica intima (i.e., the inner layer of the blood vessel). Such a suitable surface may contain collagen binding agents such as proteins, peptides, aptamers, or the like such that adhesion of the sleeve to the blood vessel is enhanced. Other agents may be profitably integrated into the internal layer 706 such as cell growth factors to promote blood vessel wall strength, anti-coagulating agents to mitigate thrombotic events, or the like.

In another embodiment, an external layer 702 may be adjacent to the inner layer of the blood vessel, as in stent-like placements of a blood vessel sleeve within a blood vessel. In these cases, the external layer 702 and/or other layers of the sleeve may contain active agents that inhibit or prevent stenosis of the vessel. For example, compounds such as antibodies that block blood cell adhesion are known to inhibit restenosis in stent placement situations (see U.S. patent publication 2002/0006401 A1 "Modulation of vascular healing by inhibition of leukocyte adhesion function").

Other active agents may also be employed to repair blood vessel weakening or injury, including, for example, vascular endothelial growth factor (VEGF), fibroblast growth factor-2, and/or sonic hedgehog protein or the like.

In another embodiment, a middle layer 704 may comprise a material that is a shape-forming material to provide a desired degree of structural stiffness or flexibility for the rapid-prototyped custom-fitted blood vessel sleeve 700.

In another embodiment, the rapid-prototyped custom-fitted blood vessel sleeve 700 may be a collapsible rapid-prototyped blood vessel sleeve that is custom-fitted for at least one blood vessel at least partly based on anatomical blood vessel data from the individual 118. As shown in FIG. 7B, FIG. 8A, and FIG. 8B, the rapid-prototyped custom-fitted blood vessel sleeve 709 and/or 800 may be structured to expand or collapse via pleats, a folding mesh structure, or other mechanical means known in the art. Alternatively, materials may be used in the manufacture of the rapid-prototyped custom-fitted blood vessel sleeve 700 that have known expansion and/or contraction properties in the human body that are known to those of skill in the art. FIG. 7B depicts a rapid-prototyped custom-fitted blood vessel sleeve 709 with pleat 710 and pleat 712 surrounding a lumen 714, and having an outer diameter 716 in a folded state. Also depicted is an unpleated portion 717 of the sleeve. Collapsibility afforded by mechanisms such as pleats may facilitate insertion or placement of the rapid-prototyped custom-fitted blood vessel sleeve 709 into the region proximal to the blood vessel 300 prior to placement of the rapid-prototyped custom-fitted blood vessel sleeve 709 around the blood vessel 300. In one embodiment, pleat 710 may serve as a location for a therapeutic health care provider 110 to cut the rapid-prototyped custom-fitted blood vessel sleeve 709 longitudinally to create a custom-fitted blood vessel sleeve opening 701 for placement of the sleeve over a blood vessel. In such an embodiment, the rapid-prototyped custom-fitted blood vessel sleeve 709 may be made without a custom-fitted blood vessel sleeve opening 701.

FIG. 8 illustrates an exemplary embodiment related to a rapid-prototyped custom-fitted blood vessel sleeve. With respect to FIG. 8A, an oblique view of a cross-section of a rapid-prototyped custom-fitted blood vessel sleeve 800 is shown. Rapid-prototyped custom-fitted blood vessel sleeve 800 is shown with lumen 804 and pleats 802. In this and similar embodiments, the pleated region may extend for only a portion of the longitudinal length of the sleeve, for example to accommodate the portion of the blood vessel from which an aneurysm protrudes. In this case, the pleated portion of the rapid-prototyped custom-fitted blood vessel sleeve 800 may be specified to expand to a certain degree to fit the aneurysm, while remainder portions of the rapid-prototyped custom-fitted blood vessel sleeve 800 are unpleated (see also FIG. 7B and unpleated portion 717), and may be tailored to the dimensions of the unaffected blood vessel adjacent to the aneurysm. It should be understood that with each of the rapid-prototyped custom-fitted blood vessel sleeves disclosed herein, a portion of the rapid-prototyped custom-fitted blood vessel sleeve may be a non-rapid-prototyped, non-custom-fitted portion. In such a case, a rapid-prototyped, custom-fitted portion may be combined with the non-rapid-prototyped, non-custom-fitted portion to make a complete sleeve. For example a pleated portion may be connected as a module to a rapid-prototyped, custom-fitted portion. Such a pleated portion or other non-rapid-prototyped, non-custom-fitted portion may be used as an off-the-shelf commodity in various sizes so as to encompass a range of needed sizes for combination with a rapid-prototyped, custom-fitted portion.

With respect to FIG. 8B, a custom-fitted blood vessel sleeve cross-section 818 is shown. In this embodiment, an alternative pleated design is shown having pleats 824, pleat 820, lumen 822, inner diameter 826, and outer diameter 828. As in the above similar embodiments, the pleated region may extend for only a portion of the longitudinal length of the sleeve, for example to accommodate the portion of the blood vessel from which an aneurysm protrudes.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve at least partly made of a smart material. Shape memory materials may include smart materials that have one or more properties that can be significantly altered in a controlled fashion by external stimuli, such as stress, temperature, moisture, pH, electric or magnetic fields. There are a number of types of smart material, some of which are already common in the art. Some examples are piezoelectric materials that produce a voltage when stress is applied; this effect also applies in the reverse manner wherein a voltage across the sample will produce stress within the sample. Suitably specified structures made from these materials can therefore be made that bend, expand, or contract when a voltage is applied.

Another example of smart materials is thermoresponsive materials (e.g., either shape memory alloys or shape memory polymers), which are materials that can hold different shapes at various temperatures. Magnetic shape memory alloys are materials that change their shape in response to a significant change in a magnetic field. pH-sensitive polymers are materials that expand or contract when the pH of the surrounding media changes. Chromogenic systems change color in response to electrical, optical or thermal changes. These include electrochromic materials, which change their colour or opacity on the application of a voltage (e.g. liquid crystal displays), thermochromic materials change in color depending on their temperature, and photochromic materials, which change colour in response to light, for example, light sensitive sunglasses that darken when exposed to bright sunlight.

Such use of smart materials in the formation of a rapid-prototyped custom-fitted blood vessel sleeve 700 may enhance the ease of application of the sleeve to the blood vessel in terms of, for example, having a flexible sleeve during the placement procedure for opening and closing of the sleeve, followed by a manipulation that may make the sleeve more rigid as a way of enhancing the support function of the sleeve around the blood vessel.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve having at least one coating. Such a coating may be placed on an internal surface or an external surface of the rapid-prototyped custom-fitted blood vessel sleeve 700, for example the surfaces of an internal layer 706 and/or an external layer 702. A coating may comprise a coating known in the art such as one or more thrombus-resistant coatings, one or more anti-coagulant coatings, one or more biocompatibility coatings, one or more biodegradable coatings, one or more durability coatings, one or more small molecule delivery coatings, and/or one or more macromolecule delivery coatings. Examples of coatings further may include coatings that release pharmaceutically active compounds over time (e.g., drug-eluting coatings such as known drug-eluting polymers), and/or adhesive coatings (e.g., biocompatible epoxyamine adhesives described in U.S. Pat. No. 6,780,510).

Other coatings may include, for example, coatings that resist build up of cellular or biomolecular debris, or microbial debris such as fungal or bacterial growth. Some known microbial resistant coatings include silver particles in a polymer matrix that are present in the matrix material preferably at a concentration of 1 ppm to 1,000 ppm, more preferably 100 ppm to 800 ppm, especially 250 ppm to 750 ppm, and most preferably 500 pm to 700 ppm relative to the total weight of the matrix material. Such a coating is described, for example, in U.S. patent publication 2007/0051366 entitled "Medical Devices With Germ-Reducing Surfaces." Such coatings may include one or more hydrophilic surfaces, one or more hydrophobic surfaces, and/or one or more surfaces that are engineered to physically repel water or other biological molecules.

Alternatively, a sleeve surface or surface coating may be a metallic nano-powder using, for example, an inert gas condensation method. This involves vaporizing the base metal in an inert gas atmosphere, after which it is deposited as a powder and then directly processed. With this method, minimal quantities of silver are sufficient to achieve the desired antibacterial properties of the powder due to its nanostructure. The nanosilver can be used to coat the surfaces of medical devices in the production process, which helps to decrease or even avoid the use of antibiotics.

Chemical nanotechnology can also be used for coating sleeve surfaces. Such self-cleaning surfaces include those with antibacterial properties. Numerous different materials, such as metal, glass, and plastics can be coated in this way. The thin, nanoporous layer also allows a great freedom of choice in terms of the shapes that can be coated.

In another embodiment, an anti-hyperplasic agent such as, for example, poly(L-lysine)-graft-poly(ethyleneglycol) (PLL-g-PEG) adsorbed to sleeve surfaces may be used to reduce neointimal hyperplasia or other blood vessel surface hyperplasia (see Billinger et al., "Polymer stent coating for prevention of neointimal hyperplasia," J. Invasive Cardiol. 2006 September; 18(9):423-6).

In some embodiments, a coating may be applied in a perioperative procedure, for example, as described in U.S. patent publication 2005/0037133 A1, entitled "Method for applying drug coating to a medical device in surgeon room."

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve having at least one of a polytetrafluoroethylene surface, a barbed surface, a metal surface, a silicon surface, or a hydrogel surface. Alternatively, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve having at least one of a GoreTex, Teflon, or titanium alloy surface.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve having a substantially mesh structure. Such a mesh structure is common in stent manufacture, allowing for expandability of the stent to a maximum limit.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve capable of shrinking to fit the blood vessel. Such a blood vessel sleeve may be made of a material with known shrinking or contraction properties in an aqueous environment such as is found in and around the vasculature, so that placement of the sleeve on a portion of a blood vessel will be accompanied by wetting of the sleeve material and shrinking of the material by a known amount, to fit the blood vessel. Examples of materials known to shrink upon insertion into an aqueous body environment include fabrics, especially when exposed to hot water. Other materials may shrink upon the attainment of body temperature, such as certain rubber materials as described in U.S. Pat. No. 6,221,447. Alternatively, elastic materials such as elastomeric polymers may be used to form the rapid-prototyped custom-fitted blood vessel sleeve 700. Such elastic materials, once tailored to closely fit the blood vessel 300, may have the added benefit of expanding and contracting with the blood vessel wall as the blood vessel diameter changes in response to temperature, vasoconstrictors, vasodilators, or other agents or situations that cause constriction and/or dilation of blood vessels. It should be understood that portions of a rapid-prototyped custom-fitted blood vessel sleeve 700 that are fitted to an aneurysm portion of a blood vessel may be specified to have limited expansion parameters so as to prevent rupture of the aneurysm. Accordingly, a portion of a rapid-prototyped custom-fitted blood vessel sleeve 700 may be made of stretchable material, whereas another portion of the rapid-prototyped custom-fitted blood vessel sleeve 700 may be made of non-stretchable material or material with limited expansion parameters.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve capable of expanding to fit the blood vessel. Materials known to expand in aqueous environments may also be used to make a rapid-prototyped custom-fitted blood vessel sleeve 700. Such materials include water-swellable materials (e.g., starch, gelatin, chitin, gum Arabic, xanthan, cross-linked albumin, cross-linked hyaluronan, and/or alginate. Other examples of water-swellable materials include collagen, cellulose derivatives, cross-linked poly(vinyl alcohol) and copolymers, cross-linked poly(vinylpirrolidone) and copolymers, poly(hydroxyethyl methacrylate), poly(ethylene glycol) and copolymers, polyacrylate, polyacrylate-co-starch, polyacrylate-co-polyacrylamide, polyacrylamide. Other water-swellable materials known to one of skill in the art may be used. For example, the hydrophilic polyurethanes and the like of U.S. Pat. No. 4,872,867; the water-swellable plastic polymers of U.S. Pat. Nos. 5,163,952 and 5,258,020; the solid absorbents of U.S. Pat. No. 5,554,180, such as copolymers of cellulose and starch, agar and polymeric acids; the water-swellable matrix materials of U.S. Pat. No. 4,460,642; and/or the water-swellable layers of U.S. Pat. Nos. 4,496,535 and 4,872,867 may be used. As described above, elastic materials such as elastomeric polymers may be used to form the rapid-prototyped custom-fitted blood vessel sleeve 700. Such elastic materials, once tailored to closely fit the blood vessel 300, may have the added benefit of expanding and contracting with the blood vessel wall as the blood vessel diameter changes in response to temperature, vasoconstrictors, vasodilators, or other agents or situations that cause constriction and/or dilation of blood vessels.

In another embodiment, the rapid-prototyped custom-fitted blood vessel sleeve 700 may be a rapid-prototyped blood vessel sleeve that is custom-fitted for a blood vessel at least partly based on anatomical blood vessel data from an individual, the rapid-prototyped blood vessel sleeve being made up of two or more modules. For example, a rapid-prototyped custom-fitted blood vessel sleeve 700 may be specified to fit a blood vessel trifurcation with an aneurysm at a blood vessel branch area, in which the rapid-prototyped custom-fitted blood vessel sleeve 700 is made up of sub-parts or modules that can be assembled, for example, during a surgical procedure to form a complete rapid-prototyped custom-fitted blood vessel sleeve 700.

In another embodiment, the rapid-prototyped custom-fitted blood vessel sleeve 700 may be a rapid-prototyped blood vessel sleeve that is custom-fitted for the blood vessel at least partly based on computer-generated anatomical blood vessel data from the individual 118. Frequently, an individual 118 with a vascular health issue will be subject to evaluation by, for example, a diagnostic health care provider 116 such as a radiologist operating medical imaging equipment that provides computer-generated anatomical blood vessel data 120. Such medical imaging may include magnetic resonance imaging (MRI scanning), computed tomography or computed axial tomography (CT scanning), positron emission tomography (PET scanning), and/or angiography. For example, a CT scan of an individual's head may provide a large series of two-dimensional images of a cross-section of the head where digital geometry processing is used to generate a three-dimensional image based on the large series of two-dimensional images. CT scanning typically produces a volume of data pertaining to the individual 118 that can be manipulated through a process known as windowing to produce an image of various internal structures based on their ability to block an x-ray beam. Other methods of visualizing blood vessel anatomy may also be used. Such a three-dimensional image, for example, provided by a CT scan process may provide anatomical blood vessel data 120, e.g., dimensions, from which a custom-fitted blood vessel sleeve may be specified.

In another embodiment, the rapid-prototyped custom-fitted blood vessel sleeve 700 may be a rapid-prototyped blood vessel sleeve that is custom-fitted for the blood vessel at least partly based on a three-dimensional anatomical model of the blood vessel from the individual 118. As noted above, an imaging system 114 often provides two-dimensional geometric images of a cross-section of an individual's anatomy (e.g., two-dimensional anatomical blood vessel data 120) and/or three-dimensional anatomical blood vessel data 120. Such anatomical blood vessel data 120 may be converted into a three-dimensional anatomical model by a three-dimensional modeling unit 104 operable on a device 102, or by software known in the art operable on a remote device. Examples of such software include amira 4 software from Mercury Computer Systems, which describes the amira 4 software as automatic and interactive segmentation tools that support rapid processing of 3D image data. Mercury Computer Systems further states that graphics hardware is efficiently utilized to display large datasets at interactive speed with unmatched image quality.

Amira 4-supported file formats include, for example, Digital Imaging and Communications in Medicine (DICOM), which is a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format. DICOM enables the integration of scanners, servers, workstations, printers, and network hardware from multiple manufacturers into a picture-archiving and communication system. The different devices come with DICOM conformance statements which clearly state the DICOM classes they support. DICOM has been widely adopted by hospitals and is making inroads in smaller applications like dentists' and doctors' offices. Other amira 4-supported file formats include, for example, JPEG image format, BMP image format, Raw data, TIFF image format, HTML, VRML, Catia4, and Catia5.

Amira 4 features include, for example, data manipulation and filtering, surface rendering, volume rendering, and data analysis to quantify densities, distances, areas, and volumes. Other features include, for example, advanced polygonal models, time-dependent data, fusion and alignment of multiple datasets, flow simulation within a 3D model, image segmentation, and surface reconstruction. The software supports reconstruction and analysis of vascular, dendritic, and fracture networks. The amira Skeletonization Pack combines specific micro-detailed image mosaics management with advanced automatic and semi-automatic tools for reconstruction of a 3D vessel network from confocal microscopy or synchrotron image acquisition.

Another three-dimensional modeling program that is commercially available is 3D-Doctor, made by Able Software Corp. 3D-Doctor is described as an advanced 3D modeling, image processing and measurement software for MRI, CT, PET, microscopy, scientific, and industrial imaging applications. 3D-Doctor is capable of exporting polygonal mesh three-dimensional models to STL (ASCII and Binary), DXF, IGES, 3DS, OBJ, VRML, PLY, XYZ and other formats for surgical planning, simulation, quantitative analysis, finite element analysis (FEA) and rapid prototyping applications. Using the program, one can calculate 3D volume and make other 3D measurements for quantitative analysis. 3D-doctor is approved by the FDA's 510 k clearance for medical imaging and 3D visualization applications. 3D-Doctor supports both grayscale and color images stored in DICOM, TIFF, Interfile, GIF, JPEG PNG, BMP, PGM, RAW or other image file formats. 3D-Doctor can create 3D surface models and volume rendering from 2D cross-section images in real time on a computer.

Accordingly, in another embodiment, the rapid-prototyped custom-fitted blood vessel sleeve 700 may be a rapid-prototyped blood vessel sleeve that is custom-fitted for the blood vessel at least partly based on a three-dimensional anatomical model of the blood vessel data from the individual, the three-dimensional anatomical model of the blood vessel from the individual at least partly derived from at least one of computed tomography data, magnetic resonance imaging data, positron emission tomography data, ultrasound imaging data, optical imaging data, or angiography data.

In a further embodiment, the rapid-prototyped custom-fitted blood vessel sleeve 700 may be a rapid-prototyped blood vessel sleeve that is custom-fitted for the blood vessel at least partly based on a three-dimensional anatomical model of the blood vessel from the individual, the three-dimensional anatomical model of the blood vessel from the individual at least partly derived from at least one of computed tomography angiography data, magnetic resonance angiography data, or Doppler ultrasound data.

Computed tomography angiography (CTA) is a medical imaging technique that uses x-rays to visualize blood flow in arterial and venous vessels throughout the body, from arteries serving the brain to those bringing blood to the lungs, kidneys, and arms and legs. CTA combines the use of x-rays with computerized analysis of the images. Beams of x-rays are passed from a rotating device through the area of interest in the patient's body from several different angles to create cross-sectional images, which then are assembled by computer into a three-dimensional picture of the area being studied. Compared to catheter angiography, which involves placing a sizable catheter and injecting contrast material into a large artery or vein, CTA is a much less invasive and more patient-friendly procedure-contrast material is injected into a small peripheral vein by using a small needle or catheter.

Magnetic resonance angiography (MRA) is an MRI study of the blood vessels. It utilizes MRI technology to provide detailed images of blood vessels without using any contrast material, although a paramagnetic contrast material such as gadolinium is often given to make the MRI images even clearer. MRA may also use a technique known as flow-related enhancement (e.g., 2D and 3D time-of-flight sequences), in which most of the signal on an image is due to blood which has recently moved into that plane. MRA may also use fast low angle shot magnetic resonance imaging (FLASH MRI).

For example, the Human Arterial Tree Project, which has a website at http://www.cfm.brown.edu/crunch/ATREE/index.html, has applied high performance computing to create three-dimensional models of portions of human arterial anatomy, such as arterial branches and the heart. The Project has developed a series of software tools that allows for the reconstruction of arterial geometry for use with the software program Nektar, a research code that is based on the spectral/hp element method developed by Karniadakis and Sherwin. It employs an unstructured finite element mesh with a spectral expansion within each element. Resolution can be increased by increasing the polynomial order (p-type refinement) of the element or by increasing the number of elements (h-type refinement). Discretization for complex geometries is efficient and achieves global spectral accuracy. A stiffly stable time stepping scheme is utilized with temporal accuracy up to third-order. Nektar is freeware and is being used by several research teams around the world.

Geometric data may be acquired, for example, by MRA and/or CT, possibly combined with injection of a contrast agent into the arteries. These are widely used approaches for accurate and non-invasive acquisition of arterial geometric structure. For example, the Human Arterial Tree Project used images of cross-sectional slices acquired by a GE LX Signa Echospeed version 9.1 MRI scanner. Acquired images can then be used to extract the contours of arteries of interest, for example, from an unrefined or refined color intensity matrix. For example, a sub-region of the artery can be interpolated onto a finer mesh where the actual contour extraction is performed. This permits sub-pixel resolution to better capture the arterial geometry. Arterial walls can be constructed by interpolating data that represent the region between extracted contours. Due to the relatively low resolution of CT and MRA images, a rough surface of the arterial wall may first be obtained, followed by a computational, alternative bi-directional smoothing process in which each contour is smoothed in the azimuthal and axial directions. This data can then be input into a series of scripts and imported into, for example, Gridjen, a commercially available mesh generator (Pointwise, Inc., Fort Worth, Tex.), to create a three-dimensional mesh representation of a portion of a blood vessel.

Elements created by mesh-generating programs such as Gridgen have flat faces. Representation of curved boundaries can be achieved by projection of element faces on the blood vessel walls. Parametric representation of arterial walls, saved in plot3D format and used for mesh generation, allows for consistent mapping of a grid from computational to physical space. Such a process has been used by the Human Arterial Tree Project to create a three-dimensional geometric model of the internal carotid artery (ICA) and an associated aneurysm. The model was constructed from 3D CTA data from a patient at Rhode Island Hospital. The model captures the curved surfaces of the blood vessels and bifurcation of the ICA into anterior communicating artery 914 and anterior cerebral artery 910.

Such a computed three-dimensional anatomical model may be used by the device 102 as a basis for custom-fitting a blood vessel sleeve to a blood vessel. As in the use of garment-fitting algorithms in which body dimensions are used to model a person to fit clothing to the person, algorithms may be used to fit a blood vessel sleeve to a blood vessel. For example, the device 102 and/or sleeve-fitting unit 106 can extract two or more sets of anatomical blood vessel data 120, each data set defining a contour of a blood vessel at least partly based on blood vessel data pertaining to an individual 118; and the sleeve-fitting unit 106 can interpolate data representing one or more regions between two or more extracted contours to define dimensions of a sleeve in the region between the two or more extracted contours. This process can then be repeated by the sleeve-fitting unit 106 until the dimensions of an entire sleeve are specified.

In another embodiment, the device 102 and/or sleeve-fitting unit 106 may scale a three-dimensional mesh model of a blood vessel by creating a transform matrix based on scale factors. The device 102 and/or sleeve-fitting unit 106 can multiply each point in the mesh model by the transform matrix. The use of matrix transformations to rotate, translate, and scale points in a three-dimensional space are well known in the apparel arts, as described in U.S. Pat. No. 5,850,222. In this way, a sleeve may be modeled after the blood vessel according to precise specifications.

In another embodiment, the device 102 and/or sleeve-fitting unit 106 can extract two or more sets of anatomical blood vessel data 120 that correspond to contours of a blood vessel at least partly based on at least one of a light intensity matrix or a color intensity matrix.

Fitting a sleeve to a blood vessel may be accomplished by mapping dimensions of a sleeve to the dimensions of a three-dimensional model of a blood vessel. In this way, the sleeve may be specified to fit the blood vessel as loosely or as tightly as deemed appropriate by a therapeutic health care provider 110, for example. Fitting a sleeve to a three-dimensional model can allow for a therapeutic health care provider 110 to closely fit a sleeve to the particular curvature, diameter and length, branching, or aneurysm dimensions of a blood vessel.

In another embodiment, a device 102 and/or sleeve-fitting unit 106 can apply a scaling factor to a three-dimensional model of a blood vessel such that sleeve dimensions or specifications are produced that are closely tailored to the blood vessel dimensions within a range of tolerance levels, for example, a percentage of the blood vessel dimensions.

Alternatively, the device 102 and/or sleeve-fitting unit 106 can assign a set of position coordinates to a three-dimensional model and assign counterpart position coordinates to a blood vessel sleeve model to produce blood vessel sleeve dimensions that fit the blood vessel.

In an alternate embodiment, the device 102 and/or sleeve-fitting unit 106 can produce sleeve specifications based on best fit criteria. In one embodiment, the best fit criteria may include specified cross-sectional dimensions. In another embodiment, the specified cross-sectional dimensions may be based on actual cross-sectional-dimensions represented by the blood vessel data. In yet another embodiment, the specified cross-sectional dimensions may be based on actual cross-sectional dimensions represented by the blood vessel data and based on tolerance criteria, e.g., 1%, 2%, 5%, or 10% variation in sleeve dimension relative to actual cross-sectional dimensions.

Various garment-fitting algorithms may be adapted to use in custom-fitting a blood vessel sleeve. For example, known garment-fitting methods such as those disclosed in U.S. Pat. No. 5,163,007, U.S. Pat. No. 5,850,222, and/or U.S. patent publication US 2004/0093105 may be employed by the sleeve-fitting unit 106 to produce custom blood vessel sleeve specifications.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve further having one or more closure means. Such closure means will ensure that the blood vessel sleeve will stay in place around the blood vessel after placement to perform its function of, for example, supporting the weakened wall of a blood vessel with an aneurysm.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve further having one or more of extensions positioned for closure, suturing tabs, detents, hooks, Velcro, or interlocking closure ridges.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve being one of a set of rapid-prototyped blood vessel sleeves. Such a set of blood vessel sleeves may be made perioperatively for use by a health care provider 110 who may want the option of having a series of different-sized sleeves for use on a patient's blood vessel during a surgery to address, for example, an aneurysm.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve being one of a set of rapid-prototyped blood vessel sleeves that each has at least one of different dimensions, a different material composition, or a different coating. Again, such a set of blood vessel sleeves may be made perioperatively for use by a therapeutic health care provider 110 who may want the option of having sleeves of varying composition, dimensions, and/or coating. The therapeutic health care provider 110 may, upon viewing surgically the actual blood vessel to be addressed, make a judgment on the spot to select a certain size or kind of sleeve depending on potential differences between the results of medical imaging and first hand observation of the blood vessel.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve being one of a set of rapid-prototyped blood vessel sleeves that each has at least different closure extensions.

In another embodiment, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve being one of a set of rapid-prototyped blood vessel sleeves of progressively increasing or progressively decreasing size.

In another embodiment, the rapid-prototyped custom-fitted blood vessel sleeve 700 may be a rapid-prototyped blood vessel sleeve that is custom-fitted for the blood vessel at least partly based on anatomical blood vessel data 120 from the individual 118, the rapid-prototyped blood vessel sleeve further having an indicator on the blood vessel sleeve. Such an indicator may aid the therapeutic health care provider 110 in, for example, tracking the blood vessel sleeve during surgery. An indicator may include a text label or numerical information, or an indicator may be a symbol or code that represents other information. Alternatively, the indicator may be a radiofrequency identification device (RFID) that contains information about the sleeve and/or the patient receiving the sleeve.

In another embodiment, the indicator on the rapid-prototyped custom-fitted blood vessel sleeve 700 may be an indicator corresponding to a size of the blood vessel sleeve. For example, where a series of different-sized sleeves is produced by rapid-prototyping, an indicator of size will aid the therapeutic health care provider 110 in choosing the correct sleeve. Similarly, the indicator on the rapid-prototyped custom-fitted blood vessel sleeve 700 may be an indicator corresponding to a material thickness of the blood vessel sleeve. Alternatively, the indicator on the rapid-prototyped custom-fitted blood vessel sleeve 700 may be an indicator corresponding to a material stiffness of the blood vessel sleeve. Or, the indicator on the rapid-prototyped custom-fitted blood vessel sleeve 700 may be an indicator corresponding to a material type of the blood vessel sleeve.

In another embodiment, the indicator on the rapid-prototyped custom-fitted blood vessel sleeve 700 may be an indicator corresponding to individual-characterizing data. Alternatively, the indicator on the rapid-prototyped custom-fitted blood vessel sleeve 700 may be an indicator corresponding to at least one of a time or a date.

In another embodiment, the indicator on the rapid-prototyped custom-fitted blood vessel sleeve 700 may be an indicator relating to a color coding of the blood vessel sleeve. As a rapid-recognition feature, color coding would allow a therapeutic health care provider 110 to quickly identify a particular feature of a custom-fitted blood vessel sleeve 112. In another embodiment, the color coding of the rapid-prototyped custom-fitted blood vessel sleeve 700 may be a color coding corresponding to patient data. In another embodiment, the color coding of the rapid-prototyped custom-fitted blood vessel sleeve 700 may be a color coding corresponding to at least one of material type, material thickness, material stiffness, sleeve size, thickness of the blood vessel sleeve, or sleeve coating.

In another embodiment, a custom-fitted blood vessel sleeve 112 may include a rapid-prototyped blood vessel sleeve that is custom-fitted for the blood vessel at least partly based on anatomical blood vessel data from the individual, the rapid-prototyped blood vessel sleeve further having at least one contrast agent within the material of the blood vessel sleeve. Doping, impregnating, embedding, or otherwise placing a contrast agent within the material composition of a custom-fitted blood vessel sleeve 112 may enhance medical imaging of the sleeve subsequent to its placement on or within a blood vessel in an individual 118. This may be useful for short-term and/or long-term follow-up of the functioning of the custom-fitted blood vessel sleeve 112 in the individual 118. For example, a sleeve containing gadolinium will appear in MRI-scanned images, and a sleeve containing iodine will appear in CT-scanned images. A custom-fitted blood vessel sleeve 112 may contain, for example, multiple contrast agents to facilitate detection of the sleeve by a number of different imaging methods.

In another embodiment, a rapid-prototyped custom-fitted blood vessel sleeve 112 may include a rapid-prototyped blood vessel sleeve that is custom-fitted for the blood vessel at least partly based on anatomical blood vessel data from the individual, the rapid-prototyped blood vessel sleeve further having at least one indicator of deformation or wear. For example, the custom-fitted blood vessel sleeve 112 may have visible grid or otherwise detectable grid of perpendicular lines on its surface, such that upon deformation or wearing of the sleeve, the right angles of the grid change to acute or obtuse angles in the area of wear or deformation. The degree and/or rate of wear and/or deformation may thus be apparent from an imaging or inspection of the indicator of deformation or wear after a period of time.

A rapid-prototyped custom-fitted blood vessel sleeve 112 may be made by rapid-prototyping in a perioperative scenario in which, for example, a therapeutic health care provider 110 obtains anatomical blood vessel data 120 from an individual 118 via an imaging system 114; using a device 102, three-dimensional modeling unit 104, and/or sleeve-fitting unit 106, the therapeutic health care provider 110 may then operate a sleeve-making device 108 to produce a custom-fitted blood vessel sleeve 112. This production of a custom-fitted blood vessel sleeve 112 may be carried out by a rapid-prototyping device, by, for example, automated two-dimensional laser-cutting of fabric or three-dimensional printing.

Accordingly, rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve further consisting essentially of laser-cutting device output. Alternatively, the rapid-prototyped custom-fitted blood vessel sleeve 700 may be a rapid-prototyped blood vessel sleeve that is custom-fitted for the blood vessel at least partly based on anatomical blood vessel data from the individual, the rapid-prototyped blood vessel sleeve further consisting essentially of three-dimensional printer output.

Rapid-prototyping may include additive fabrication, three-dimensional printing, solid freeform fabrication, and/or layered manufacturing. With rapid-prototyping, objects can be formed with any geometric complexity or intricacy without the need for elaborate machine setup or final assembly; and objects can be made from multiple materials, as composites, and/or materials can be varied in a controlled fashion at any location in an object.

Examples of known rapid-prototyping devices and methods may include use of a stereolithography apparatus, which uses a UV laser to trace a cross-section of the product model layer by layer across the top of a vat of liquid polymer. This then hardens a thin layer of the material. As each layer is traced, the object is lowered slightly for the laser to trace the next cross-section of the object in the polymer, solidifying that layer and bonding it to the previous layer. This is done layer by layer until the object is formed. Another method is selective laser sintering, which uses a laser to fuse (i.e., sinter) a thin layer of powdered material into a solid object. After each layer is completed, a thin layer of the powdered material is spread across the top for the fusing of the next layer. This is a good method for fine detail and thin-walled parts.

Another rapid-prototyping method is fused deposition modeling, which uses a temperature-controlled head to extrude and deposit thermoplastic material based on computer-aided drafting (CAD) cross-section slices. The material starts in a semi-liquid state, bonds to the previous solid layer, and then hardens. Another method is solid ground curing, which prints each CAD cross-section slice on a glass photomask using a electrostatic process like a photocopier. An ultraviolet light shines through the mask onto a thin layer of polymer, hardening the exposed resin. Residual liquid resin is vacuumed off and a liquid wax is spread onto any spaces. This layer is cooled to a solid and then milled to thickness. Repeating the process with the next layer builds up the part.

Laminated object manufacturing starts with a thin layer (4 to 8 millimeters) of sheet material and uses a laser to cut a first CAD pattern based on a cross-section. A blank sheet backed with a dry adhesive is then rolled across the cut layer and heat-bonded. The cutting process begins again on that sheet. This process builds parts with relatively thick walls.

Inkjet Technology deposits tiny droplets of hot liquid thermoplastic in a desired pattern, layer by layer. Droplets of material may generate a support structure that is later melted away, dissolved or physically removed.

Direct shell production casting produces ceramic casting molds for metal casting using a layered printing process depositing a liquid binder onto a layer of ceramic powder. After the mold is "printed," it is then fired. These molds will handle any metal and are more accurate than those made from sand casting.

Direct metal deposition uses a CNC laser to fuse layers of metal powder. The resulting prototypes made from H13 tool steel, aluminum and other metals are suitable for use in production.

Precision metal deposition, or PMD, flat wire metal deposition technology uses an energy source such as a laser, to fuse a solid metal flat wire to a substrate.

3D Printing is a term that describes several similar technologies for machines that often operate in an office-like setting. An inkjet system may be used to print glue onto layers of loose ceramic (alumina) powder to build casting molds or appearance models. A liquid binder material with powdered metal may also be printed.

Rapid-prototyping can produce sleeves made of, for example, thermoplastics and eutectic metals (fused deposition modeling), photopolymer (stereolithography and multi-jet modeling), paper (laminated object manufacturing), Titanium alloys (electron beam melting), and various polymers and other materials (3D Printing).

Automated fitting systems and rapid-prototyping systems have been developed in the textile and apparel industry. For example, the clothing industry has developed body scanners that perform body imaging functions that are similar to the medical imaging functions of medical imaging devices. According to the clothing industry, because an image of the body is captured during the scanning process, the location and description of the measurements can be altered as needed in mere seconds. Also, the measurements obtained using this technology have the potential of being more precise and reproducible than measurements obtained through the physical measurement process. Further, with the availability of an infinite number of linear and non-linear measurements the possibility exists for garments to be created to mold to the 3 dimensional shapes of unique human bodies. Finally, body-scanning technology allows measurements to be obtained in a digital format that can integrate automatically into apparel CAD systems without the human intervention that takes additional time and can introduce error. These benefits from the apparel industry may be applied to the specification and manufacture of custom-fitting blood vessel sleeves as well.

Textile or apparel systems for clothing specification and/or rapid production include the following examples. Assyst/Bullmer, Inc. has an array of products that have been developed to support rapid product creation. Product functions include pattern making and grading; sketching, design, and draping; automated pattern making; automated marker making; data conversion and exchange; sewing plan generation; cut order planning; plotting, milling, and routing; automated material handling; automated fabric spreading; and automated material cutting.

Cad.assyst from Assyst/Bullmer, Inc. is an apparel pattern development and modification software program. It includes software for pattern design, grading, and marker making/nesting. The system enables one to digitize patterns into the system, or create pattern pieces directly on a display, grade them, and create markers. With this program, many pattern pieces can be worked on simultaneously, without restrictions. One feature is pattern dependency that allows any changes made on a source pattern to also occur on the patterns created from it. Macros can be easily created for repetitive tasks, such as the addition of seam allowances, the creation of facings, and the placement of buttons and buttonholes. Piece and grading information can be imported from Gerber, Lectra, PAD, or any other program that can export using the AAMA .dxf file format. Such a system may be developed for specifying a custom blood vessel sleeve, such that a sleeve pattern may be created based on anatomical blood vessel data 120 from an individual 118. Such a blood vessel sleeve pattern may be manipulated in an electronic system to achieve desired measurements and/or manufacturing specifications.

One can grade using standard x/y and distance grading within rule tables. Or one can perform visual, direct modifications to pattern shapes on individual sizes. Modifications are automatically recorded in the grade table and there are no size display limitations. Piece grading is automatically recalculated whenever a piece is modified, scaled, mirrored, rotated, or split. Using the flexible measure grading function, one can measure and compare the graded lines and curves of multiple pieces. Accordingly, a blood vessel sleeve pattern based on anatomical blood vessel data 120 from an individual 118 may be graded according to the judgment of a therapeutic health care provider 110 or other health care provider.

With cad.assyst, a seam allowance feature supports all pattern design and production process requirements. Any change of the piece design contour will automatically adjust the seam and hem lines. Seams can be hidden while modifying or grading pieces. Also, the pleat functionality supports all known pleat variations in the apparel industry. One can modify pattern pieces with open or closed pleats. Accordingly, seam and/or pleat characteristics of a rapid-prototyped custom-fitted blood vessel sleeve 800 may be specified and/or manufactured according to the above known functions of the apparel industry.

A dart feature allows one to reposition and make modifications to the piece contour whether the dart is open or closed. Hatching allows one to develop sewing plans, which can be sent to individual production facilities and to external information systems. A stitch-counting feature supports the development of pattern data for flat-form knitting. This function calculates for each size the x/y number of knits with recognition of the shrinkage factor. The information is exported in an interface file and can be transferred to known stitching machines. A grade line allows grading of any created curve or line in the pattern piece. Such grading may be useful in making a set of custom-fitted blood vessel sleeves of varying dimensions for use by a therapeutic health care provider 110 or other health care provider in an operative setting or a perioperative setting. In such an instance, as discussed above, a health care provider 224 may select an appropriate custom-fitted blood vessel sleeve 406 from among a set of custom-fitted blood vessel sleeves 506, according to an actual view of a blood vessel to be addressed or other anatomical features of an area proximate to an affected blood vessel. For example, to minimize frictional contact of a custom-fitted blood vessel sleeve 406 with a nearby organ, blood vessel, or other structure, a therapeutic health care provider 110 or other health care provider may select a custom-fitted blood vessel sleeve that is, for example, thinner along one axis, shorter along one axis, and/or composed of a different material in a certain portion of the sleeve.

Smart.pattern is a program that is a modification tool rather than a construction tool. The purpose of this software is to automate work done repeatedly by creating macros that are organized by type of activity. Compound macros can also be created to work together. The system has 500 pre-defined modules that can be used to easily create a background macro. After training, a user can create her own modules for activities not initially covered. Leonardo is a program for managing made-to-measure or custom products. The system is made up of three parts that recreate a specific pattern based on defined measurements. This program affords faster specification of garments made from different combinations of body measurements. Such a system may be applied to modifying custom-fitted blood vessel sleeve patterns once created based on anatomical blood vessel data 120 from an individual 118.

Gerber Technology's PDS 2000 allows the user to move multiple lines at once, in the same direction, or in reverse, as desired. The system can also remember where pieces were on the screen when they were saved so that they can return to that position when recalled. Multiple pieces can be selected at one time using the marquis function. Pieces can also come into the work area in a full-scale view. This allows patterns to be created or refined in less time. Accordingly multiple custom-fitted blood vessel sleeves may be specified concurrently.

APDS 3D is software from Asahi that allows a virtual try-on of garments created in PDS 2000. This system comes with a variety of dress forms—men's, ladies', children's, Juniors, and with legs—all of which can be altered by the user, to some degree. An ease table is built into the system, which allows fabric drape to be demonstrated based on Kawabata values. Essentially, this software allows the user to drape 2D patterns on-screen and make pattern revisions, check new designs and graded patterns on a virtual drape model, and input fabric design to create a virtual sample. Such a system adapted for use with a custom-fitted blood vessel sleeve specification system can model a custom-fitted blood vessel sleeve over a virtual blood vessel to simulate fit of the custom-fitted blood vessel sleeve.

INVESTRONICA SISTEMAS has introduced a 3D system from an alliance with Toyobo called Dressing Sim FDK. This system acts as a virtual try-on of garments created through the Pattern Generation System (PGS). The user will import a body form, import a pattern created in PGS, and import pattern characteristics. After lining each garment piece up to the body, it can be evaluated from each side of the body. Once properly aligned, the garment will be virtually seamed together. Fabric variations can be applied to simulate fabric drape and relaxed to conform to the body. As above for the APDS 3D software, such a system adapted for use with a custom-fitted blood vessel sleeve specification system can model custom-fitted blood vessel sleeve patterns over a virtual blood vessel to simulate fit of the custom-fitted blood vessel sleeve.

Another product is the 3D-Design system, which has 50 to 60 body shapes to cover a wide range of ages, sizes, and shapes of people. The user will also have the ability to change the measurements of the key dimensions, as desired. INVESTRONICA handles the issue of ease in their Body Garment 3D Design system by allowing the user to define the specific amount of ease desired in specific locations. Once the ease layer has been defined, the designer will be able to draw design lines on the 3 dimensional form. These lines will then be used to identify pattern shapes that will be flattened to 2D for export into their PGS system. Such a system adapted for use with a custom-fitted blood vessel sleeve specification system can model a custom-fitted blood vessel sleeve, including layers in the case of multiple-layered sleeves.

3D Sample software allows a two-dimensional set of patterns to be placed on a 3D form that is the correct size for a virtual try-on of the virtually sewn garment. The user can also create a technical drawing of the garment, export it to Adobe Illustrator and/or a pattern file. If the garment is too small to fit correctly, body parts will show through. Such a virtual try-on system can also be adapted to a custom-fitted blood vessel sleeve specification system such that a sleeve fitted to a blood vessel can be visualized in order to, for example, select the correct size of sleeve.

Many CAD systems used in apparel pattern-making have some method that enables pattern alterations based on individual measurements. Many, including those from Gerber Technologies, Lectra Systems, Investronica, and Assyst, have three preparational activities in common that allow automatic alterations to be made. These preparational activities allow the automatic alteration of existing garment patterns. This set of activities requires a knowledge of garment design, grading, and garment construction, as well as an understanding of computer programming. Developers have been working to integrate measurements extracted from three-dimensional body scanners in the garment specification process. Such expertise can be adapted for use with a custom-fitted blood vessel sleeve specification system to model a custom-fitted blood vessel sleeve.

In one embodiment, an alteration rule table can be created, as is done with the Gerber Accumark system. Such an alteration rule table can be created according to how the structural lines of the garment should move based on the difference between actual body measurements of the subject and the physical measurement upon which the sizing grade was based at key locations. Key measurement locations for a fitted shirt, for example, include the bust, waist, hip, backwaist length, and waist height. Alteration rules can be created much like grade rules in that the grading movement may be significant to the orientation of the pattern piece on the computer screen. As adapted to a custom-fitted blood vessel sleeve specification system, blood vessel measurements such as diameter, curvature, branching, aneurysm dimensions, or the like can be applied to an alteration rule table according to how the structural lines of the sleeve should move based on known movement of the blood vessel during systole and diastole, or based on simulated movement of the blood vessel during various blood circulation events.

Once a garment is graded and prepared for alteration, the accuracy of the alteration decisions can be evaluated. To do this, the garment is often compared to a three-dimensionally scanned body of a test subject. This can be done by extracting the key measurements needed for each garment, and physically inserting those measurements within the size code tables in, for example, the Gerber Accumark System. A customized marker can be made for each garment using the grade rule, alteration, and size code tables developed. The garments can then be fit-tested on a test subject. A similar process may be performed by the sleeve-fitting unit 106 in comparing a custom-fitted sleeve, custom-fitted sleeve pattern, or standard sleeve pattern to a three-dimensionally scanned blood vessel of an individual 118. The sleeve-fitting unit 106 may then extract the key measurements needed for the custom-fitted blood vessel sleeve and insert the extracted measurements within a size table. A customized marker can then be made for each sleeve using grade rule, alteration, and size code tables.

Similarly, a custom-fitted blood vessel sleeve may be specified based custom-fitting techniques, grade rules, and/or alteration rules such as those that have been developed and used in the field of garment specification, described above. Just as clothing makers can specify a tailored joining of a body tube of a specific proportion for an individual 118 with sleeve tubes of a specific proportion for the individual, a device 102 and/or sleeve-fitting unit 106 can join, for example, a sleeve portion corresponding to the specific anatomy of a blood vessel 400 with a sleeve portion corresponding to the specific anatomy of a blood vessel branch 404 together with the juncture where the two meet and any specific aneurysm anatomy that may be present on the blood vessel 400 and/or blood vessel branch 404.

Similarly, a custom-fitted blood vessel sleeve 406 may be specified that is capable of fitting a complex blood vessel junction. For example, FIG. 9 illustrates the blood vessel anatomy of the Circle of Willis 900, a complex of arteries in the area of the inferior surface of the brain surrounding the pituitary gland where aneurysms are commonly found, and where a custom-fitted blood vessel sleeve 406 may be employed.

For example, a custom-fitted blood vessel sleeve 406 may be fitted to aneurysms 902 that are in proximity to each other on the internal carotid complex 908. Alternatively, a custom-fitted blood vessel sleeve 406 may be specified to fit aneurysms 906 near a trifurcation 912 in the region of the middle cerebral artery 916, or a four-way junction such as that near the anterior communicating artery 914 and the anterior cerebral artery 910. Alternatively, a custom-fitted blood vessel sleeve 406 may be specified to fit an aneurysm 904 near a five-way junction at the internal carotid complex 908. Accordingly, blood vessel sleeves may be specified to fit any blood vessel and/or aneurysm anatomy.

Further, known garment-fitting algorithms may be employed to alter a stock or standard blood vessel sleeve pattern to fit an individual's anatomy, based on specific anatomical blood vessel data 120 for the individual 118.

FIG. 10 illustrates the blood vessel anatomy of the abdominal aorta, similar to FIG. 6. In the embodiment of FIG. 10, a rapid-prototyped custom-fitted blood vessel sleeve 1002 has been placed on the interior aspect of the abdominal aorta to funnel bloodflow through the region affected by the abdominal aortic aneurysm 1000. Additionally, a distal portion of the rapid-prototyped custom-fitted blood vessel sleeve 1002 may be bifurcated to match the anatomy of the abdominal aorta at the junction of the aorta with the right and left common iliac arteries. Such an interior rapid-prototyped custom-fitted blood vessel sleeve 1002 may be placed within an affected blood vessel via a catheterization procedure, for example, via a femoral artery of the leg. In such cases, a collapsible rapid-prototyped custom-fitted blood vessel sleeve 1002 may be conveniently inserted into a catheter, guided to the affected portion of the abdominal aorta, and then expanded to fit, for example, the affected portion of the abdominal aorta.

FIG. 11 illustrates a portion of the blood vessel anatomy of the Circle of Willis, where a custom-fitted blood vessel sleeve 406 may be employed. In FIG. 11, a rapid-prototyped custom-fitted blood vessel sleeve 1102 has been placed on the interior aspect of the junction of the anterior communicating artery 1114 and the anterior cerebral artery 1110. Shown in FIG. 11 is an aneurysm 1104 at the junction; the rapid-prototyped custom-fitted blood vessel sleeve 1102 can be seen to block blood flow into the aneurysm 1104 from the inside of the anterior communicating artery 1114. Further, the branched nature of the rapid-prototyped custom-fitted blood vessel sleeve 1102 in this example may serve an anchoring function to help keep the rapid-prototyped custom-fitted blood vessel sleeve 1102 in place, in proximity to the affected portion of the anterior communicating artery 1114.

Although a therapeutic health care provider 110 is shown/described herein as a single illustrated figure, those skilled in the art will appreciate that a therapeutic health care provider 110 may be representative of a human health care provider, a robotic health care provider (e.g., computational entity), and/or substantially any combination thereof (e.g., a health care provider may be assisted by one or more robotic agents). In addition, a therapeutic health care provider 110, as set forth herein, although shown as a single entity may in fact be composed of two or more entities. Those skilled in the art will appreciate that, in general, the same may be said of "sender" and/or other entity-oriented terms as such terms are used herein.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

All of the above U.S. patents, U.S. patent application publications, U.S. patent applications, foreign patents, foreign patent applications and non-patent publications referred to in this specification and/or listed in any Application Data Sheet are incorporated herein by reference, to the extent not inconsistent herewith.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

What is claimed is:

1. A blood vessel sleeve comprising:
at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual, wherein the at least one curvature and the at least one distention are customized based on three-dimensional anatomical data of the at least one blood vessel portion of the individual.

2. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one curvature that conforms to blood vessel curvature of at least one aorta or cerebral artery portion of an individual and (ii) at least one distention that accommodates at least one aneurysm of the at least one aorta or cerebral artery portion of the individual when the at least one elongated portion is positioned on the at least one aorta or cerebral artery portion of the individual with the at least one curvature of the at least one elongated portion coinciding with the blood vessel curvature of the at least one aorta or cerebral artery portion of the individual.

3. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one branch portion, (ii) at least one curvature that conforms to blood vessel curvature of at least one blood vessel portion of an individual, and (iii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual.

4. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one multi-layered elongated portion having (i) at least one curvature that conforms to blood vessel curvature of at least one blood vessel portion of an individual and (ii) at least one distention that accommodates at least one aneurysm of the at least one blood vessel portion of the individual when the at least one multi-layered elongated portion is positioned on the at least one blood vessel portion of the individual with the at least one curvature of the at least one multi-layered elongated portion coinciding with the blood vessel curvature of the at least one blood vessel portion of the individual.

5. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one collapsible portion having (i) at least one curvature that conforms to blood vessel curvature of at least one blood vessel portion of an individual and (ii) at least one distention that accommodates at least one aneurysm of the at least one blood vessel portion of the individual when the at least one collapsible portion is positioned on the at least one blood vessel portion of the individual with the at least one curvature of the at least one collapsible portion coinciding with the blood vessel curvature of the at least one blood vessel portion of the individual.

6. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one substantially transparent elongated portion having (i) at least one curvature that conforms to blood vessel curvature of at least one blood vessel portion of an individual and (ii) at least one distention that accommodates at least one aneurysm of the at least one blood vessel portion of the individual when the at least one substantially transparent elongated portion is positioned on the at least one blood vessel portion of the individual with the at least one curvature of the at least one substantially transparent elongated portion coinciding with the blood vessel curvature of the at least one blood vessel portion of the individual.

7. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one biocompatible elongated portion having (i) at least one curvature that conforms to blood vessel curvature of at least one blood vessel portion of an individual and (ii) at least one distention that accommodates at least one aneurysm of the at least one blood vessel portion of the individual when the at least one biocompatible elongated portion is positioned on the at least one blood vessel portion of the individual with the at least one curvature of the at least one biocompatible elongated portion coinciding with the blood vessel curvature of the at least one blood vessel portion of the individual.

8. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one smart material-based elongated portion having (i) at least one curvature that conforms to blood vessel curvature of at least one blood vessel portion of an individual and (ii) at least one distention that accommodates at least one aneurysm of the at least one blood vessel portion of the individual when the at least one smart material-based elongated portion is positioned on the at least one blood vessel portion of the individual with the at least one curvature of the at least one smart material-based elongated portion coinciding with the blood vessel curvature of the at least one blood vessel portion of the individual.

9. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one coated elongated portion having (i) at least one curvature that conforms to blood vessel curvature of at least one blood vessel portion of an individual and (ii) at least one distention that accommodates at least one aneurysm of the at least one blood vessel portion of the individual when the at least one coated elongated portion is positioned on the at least one blood vessel portion of the individual with the at least one curvature of the at least one coated elongated portion coinciding with the blood vessel curvature of the at least one blood vessel portion of the individual.

10. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one drug-eluting portion, (ii) at least one curvature that conforms to blood vessel curvature of at least one blood vessel portion of an individual, and (iii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual.

11. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one substantially mesh elongated portion having (i) at least one curvature that conforms to blood vessel curvature of at least one blood vessel portion of an individual and (ii) at least one distention that accommodates at least one aneurysm of the at least one blood vessel portion of the individual when the at least one substantially mesh elongated portion is positioned on the at least one blood vessel portion of the individual with the at least one curvature of the at least one substantially mesh elongated portion coinciding with the blood vessel curvature of the at least one blood vessel portion of the individual.

12. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one shrinkable elongated portion having (i) at least one curvature that conforms to blood vessel curvature of at least one blood vessel portion of an individual and (ii) at least one distention that accommodates at least one aneurysm of the at least one blood vessel portion of the individual when the at least one shrinkable elongated portion is positioned on the at least one blood vessel portion of the individual with the at least one curvature of the at least one shrinkable elongated portion coinciding with the blood vessel curvature of the at least one blood vessel portion of the individual.

13. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one expandable elongated portion having (i) at least one curvature that conforms to blood vessel curvature of at least one blood vessel portion of an individual and (ii) at least one distention that accommodates at least one aneurysm of the at least one blood vessel portion of the individual when the at least one expandable elongated portion is positioned on the at least one blood vessel portion of the individual with the at least one curvature of the at least one expandable elongated portion coinciding with the blood vessel curvature of the at least one blood vessel portion of the individual.

14. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one modular elongated portion having (i) at least one curvature that conforms to blood vessel curvature of at least one blood vessel portion of an individual and (ii) at least one distention that accommodates at least one aneurysm of the at least one blood vessel portion of the individual when the at least one modular elongated portion is positioned on the at least one blood vessel portion of the individual with the at least one curvature of the at least one modular elongated portion coinciding with the blood vessel curvature of the at least one blood vessel portion of the individual.

15. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one closure mechanism, (ii) at least one curvature that conforms to blood vessel curvature of at least one blood vessel portion of an individual, and (iii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual.

16. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one extension, (ii) at least one curvature that conforms to blood vessel curvature of at least one blood vessel portion of an individual, and (iii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual.

17. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one indicator, (ii) at least one curvature that conforms to blood vessel curvature of at least one blood vessel portion of an individual, and (iii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual.

18. The blood vessel sleeve of claim 17, wherein the at least one indicator comprises:

at least one indicator corresponding to size.

19. The blood vessel sleeve of claim 17, wherein the at least one indicator comprises:

at least one indicator corresponding to thickness.

20. The blood vessel sleeve of claim 17, wherein the at least one indicator comprises:

at least one indicator corresponding to stiffness.

21. The blood vessel sleeve of claim 17, wherein the at least one indicator comprises:

at least one indicator corresponding to type.

22. The blood vessel sleeve of claim 17, wherein the at least one indicator comprises:

at least one indicator corresponding to the individual.

23. The blood vessel sleeve of claim 17, wherein the at least one indicator comprises:

at least one indicator corresponding to time or date.

24. The blood vessel sleeve of claim 17, wherein the at least one indicator comprises:

at least one indicator corresponding to deformation.

25. The blood vessel sleeve of claim 17, wherein the at least one indicator comprises:

at least one indicator corresponding to wear.

26. The blood vessel sleeve of claim 17, wherein the at least one indicator comprises:

at least one color indicator.

27. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one contrast agent, (ii) at least one curvature that conforms to blood vessel curvature of at least one blood vessel portion of an individual, and (iii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual.

28. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one customized length, (ii) at least one curvature that conforms to blood vessel curvature of at least one blood vessel portion of an individual, and (iii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual.

29. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one customized diameter, (ii) at least one curvature that conforms to blood vessel curvature of at least one blood vessel portion of an individual, and (iii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual.

30. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one curvature that conforms to blood vessel curvature of at least one blood vessel portion of an individual and (ii) at least one expandable distention portion configured to accommodate at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual.

31. The blood vessel sleeve of claim 1, wherein the at least one elongated portion having (i) at least one curvature that conforms to blood vessel curvature of at least one blood vessel portion of an individual and (ii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual comprises:

at least one elongated portion having (i) at least one inducibly modifiable portion, (ii) at least one curvature that conforms to blood vessel curvature of at least one blood vessel portion of an individual, and (iii) at least one distention that accommodates at least one aneurysm of the at least one blood vessel portion of the individual when the at least one elongated portion is positioned on the at least one blood vessel portion of the individual with the at least one curvature of the at least one elongated portion coinciding with the blood vessel curvature of the at least one blood vessel portion of the individual.

32. The blood vessel sleeve of claim 1, wherein the at least one curvature and the at least one distension are customized based on three-dimensional anatomical data of the at least one blood vessel portion of the individual comprises:

wherein the at least one curvature and the at least one distension are customized based on computer-generated three-dimensional anatomical data of the at least one blood vessel portion of the individual.

* * * * *